US009574176B2

(12) United States Patent
Miyamoto et al.

(10) Patent No.: US 9,574,176 B2
(45) Date of Patent: Feb. 21, 2017

(54) NEURAL STEM CELL HAVING INCREASED PASSAGE ABILITY, METHOD FOR MANUFACTURING NEURAL STEM CELL HAVING SAID INCREASED PASSAGE ABIILITY, AND METHOD FOR CULTURING NEURAL STEM CELLS FOR INCREASING PASSAGE ABILITY OF NEURAL STEM CELLS

(71) Applicant: Eisai R&D Management Co., Ltd., Tokyo (JP)

(72) Inventors: Norimasa Miyamoto, Tsukuba (JP); Yuichi Ono, Kobe (JP); Kana Namiki, Kobe (JP); Yoshitoshi Kasuya, Chiba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/436,206

(22) PCT Filed: Oct. 29, 2013

(86) PCT No.: PCT/JP2013/079200
§ 371 (c)(1),
(2) Date: Apr. 16, 2015

(87) PCT Pub. No.: WO2014/069431
PCT Pub. Date: May 8, 2014

(65) Prior Publication Data

US 2015/0275173 A1 Oct. 1, 2015

(30) Foreign Application Priority Data

Oct. 31, 2012 (JP) ................................ 2012-241366

(51) Int. Cl.
*A61K 48/00* (2006.01)
*C12N 5/00* (2006.01)
*C12N 5/08* (2006.01)
*C12N 5/0797* (2010.01)
*C12N 15/85* (2006.01)

(52) U.S. Cl.
CPC ............. *C12N 5/0623* (2013.01); *C12N 15/85* (2013.01); *C12N 2500/14* (2013.01); *C12N 2501/40* (2013.01); *C12N 2501/405* (2013.01); *C12N 2501/998* (2013.01); *C12N 2506/00* (2013.01); *C12N 2510/00* (2013.01)

(58) Field of Classification Search
CPC ... C12N 15/85; C12N 5/0623; C12N 2500/14; C12N 2501/40; C12N 2501/405; C12N 2501/998; C12N 2506/00; C12N 2510/00
USPC ........................ 435/368, 375, 377; 424/93.2
See application file for complete search history.

(56) References Cited

U.S. PATENT DOCUMENTS

| | | | |
|---|---|---|---|
| 7,067,714 | B1 | 6/2006 | Ino et al. |
| 2006/0035373 | A1 | 2/2006 | Zhang et al. |
| 2012/0107934 | A1 | 5/2012 | Poole |

FOREIGN PATENT DOCUMENTS

| | | |
|---|---|---|
| EP | 1240823 | 9/2002 |
| JP | 200318945 | 1/2003 |
| JP | 2007105046 | 4/2007 |
| WO | WO 01/30137 | 5/2001 |
| WO | WO 03/035698 | 5/2003 |

OTHER PUBLICATIONS

Lipscombe et al., 2006, US 20060135751 A1.*
Arnhold, S. et al., “Embryonic stem-cell derived neurons express a maturation depending pattern of voltage-grated calcium channels and calcium-binding proteins”, Int. J. Devl. Neuroscience (2000), 18:201-212.
Carpenter, M.K. et al., “In Vitro Expansion of a Multipotent Population of Human Neural Progenitor Cells”, Exp. Neurol. (1999), 158:265-278.
Emsley, J.G. et al., Adult neurogenesis and repair of the adult CNS with neural progenitors, precursors, and stem cells, Prog. Neurobiol. (2005), 75:321-341.
Ming, G. et al., “Adult Neurogenesis in the Mammalian Central Nervous System”, Ann. Rev. Neurosci. (2005), 28:223-250.
Pollard, S.M. et al., “Adherent Neural Stem (NS) Cells from fetal and Adult Forebrain”, Cereb. Cortex (2006) 16:i112-i120.
Reynolds, B.A. et al., “Generation of Neurons and Astrocytes from Isolated Cells of the Adult Mammalian Central Nervous System”, Science (1992), 255:1707-1710.
International Search Report dated Jan. 28, 2014 in corresponding PCT Application No. PCT/JP2013/079200, 4 pages.
Gil-Perotín, S. et al., “Adult Neural Stem Cells From the Subventricular Zone: A Review of the Neurosphere Assay”, The Anatomical Record, 296(9):1435-52 (2013).
Sun, Y. et al., “Long-Term Tripotent Differentiation Capacity of Huma Neural Stem (NS) Cells in Adherent Culture”, Mol. Cell. Neurosci. 38:245-58 (2008).
Supplementary European Search Report issued in EP Application No. 13851107.6, dated Mar. 17, 2016, 8 pages.

* cited by examiner

*Primary Examiner* — Shin Lin Chen
(74) *Attorney, Agent, or Firm* — Fish & Richardson P.C.

(57) ABSTRACT

The present invention provides a neural stem cell having increased passage ability and a method for manufacturing a neural stem cell having increased passage ability. A neural stem cell in which the N-type calcium channel gene is knocked out or the influx of Ca2+ via the N-type calcium channel is substantially absent can be passaged for at least 4 generations and maintains the differentiation potential into a nerve cell even after passage for 4 generations.

12 Claims, 9 Drawing Sheets

10d after 5th passage

NEURAL STEM CELL HAVING INCREASED PASSAGE ABILITY, METHOD FOR MANUFACTURING NEURAL STEM CELL HAVING SAID INCREASED PASSAGE ABIILITY, AND METHOD FOR CULTURING NEURAL STEM CELLS FOR INCREASING PASSAGE ABILITY OF NEURAL STEM CELLS

TECHNICAL FIELD

The present invention relates to (1) a neural stem cell having increased passage ability (sometimes referred to as "enhanced passage proliferation ability"), (2) a method for manufacturing a neural stem cell having said increased passage ability, (3) a method for culturing neural stem cells for increasing the passage ability of neural stem cells, (4) the use of an agent in the culturing of neural stem cells for increasing the passage ability of neural stem cells, and the like.

More specifically, the present invention, in one aspect, relates to a neural stem cell having increased passage ability having the following characteristics:

(a) the N-type calcium channel gene is knocked out or knocked down in said cell, (b) the influx of Ca2+ via the N-type calcium channel is (1) substantially absent when the N-type calcium channel gene is knocked out, or (2) suppressed when the N-type calcium channel gene is knocked down in said cell, (c) said cell can be passaged for at least 4 generations (more preferably 15 generations) or more, and (d) said cell maintains the differentiation potential into a nerve cell even after passage for 4 generations (more preferably 15 generations).

BACKGROUND ART

It has been conventionally thought that regeneration of the central nervous system does not occur. However, the repent discovery of endogenous neural stem cells in adult brain has pointed out a possibility that nerve regeneration occurs even in a matured brain. For example, constitutive neurogenesis by neural stem cells has been previously shown in the subventricular/olfactory nervous system and the hippocampal dentate gyrus of an adult rat brain. Moreover, it is known that along with brain lesion, neural stem cells appear and proliferate at other sites such as the cerebral neocortex or the striatum, and therapeutic application of these neural stem cells that appeared and proliferated to cerebrospinal damage or neurodegenerative disease etc. is greatly expected (Non-Patent Literatures 1 and 2).

Animal neural stem cells are known to differentiate into nerve cells and glial cells (astrocytes and oligodendrocytes) (multipotency). Moreover, animal neural stem cells can reproduce cells hang the same multipotency by division (self-renewal ability).

Animal neural stem cells can be employed for regenerative medicine (such as transplantation therapy), and can also be employed as an assay tool (such as an assay tool for exploring differentiation control system). Accordingly, animal neural stem cells have gathered a great deal of attention, and various analyses are being performed on animal neural stem cells.

Animal neural stem cells can be cultured by adding a proliferative factor (EGF, FGF) (Non-Patent Literatures 3 and 4). When animal neural stem cells are employed for regenerative medicine or employed as an assay tool, (1) maintenance of the ability to be able to proliferate ("self-propagation ability" or simply "proliferation ability") or (2) maintenance of the ability to be able to produce nerve cells by differentiation induction ("differentiation potential into a nerve cell") and the like are essential.

However, neural stem cells are generally known with repeated passaging to (1) have reduced self-propagation ability, as well as (2) lose its differentiation potential into a nerve cell and become more prone to being differentiated into glial cells (Non-Patent Literature 5). Accordingly, a technology for continued passage of neural stem cells for a longer generation while maintaining both "self-propagation ability" and "differentiation potential into a nerve cell" is essential.

A non-human genetically modified animal having the N-type calcium channel gene knocked out is known. It is also known that said animal is employed for screening agents involved in the control of blood pressure, transmission of pain, control of blood glucose level, and the like (Patent Literatures 1 and 2). Inhibition of the function or expression of the N-type calcium channel in neural stem cells with an inhibitor to verify the inhibition state of neural activity is also known (Non-Patent Literature 6).

CITATION LIST

[Patent Literature 1] International Publication (WO/2001/030137)

[Patent Literature 2] Japanese Published Unexamined Patent Application Publication No. 2007-105046

[Non-Patent Literature 1] Ming G, Song H. Adult neurogenesis in the mammalian central nervous system Ann Rev Neurosci 2005; 28:223-250.

[Non-Patent Literature 2] Emsley J G; Mitchell B D, Kempermann G, Macklis J D. Adult neurogenesis and repair of the adult CNS with neural progenitors, precursors, and stem cells. Prog Neurobiol 2005; 75:321-341.

[Non-Patent Literature 3] Reynilds B et al. Generation of neurons and astrocytes from isolated cells of the adult mammalian central nervous system. Science 1992, 255, 1707-1710.

[Non-Patent Literature 4] Steven M. Pollard et al. Adherent neural stem (NS) cells from fetal and Adult forebrain. Cereb. Cortex 2006:16:112-120.

[Non-Patent Literature 5] Melissa K. et al. In vitro expansion of a multipotent population of human neural progenitor cells. Exp. Neurol. 1999:158:265-278.

[Non-Patent Literature 6] Stefan A. Embryonic Stem-cell derived neurons express a maturation dependent pattern of voltage-gated calcium channels and calcium-binding proteins. Int. J. Devl Neuroscience 2000:18:201-212.

SUMMARY OF THE INVENTION

Problems to be Solved by the Invention

The present invention has been achieved in light of such a situation, and the problem it aims to solve is to provide (1) a neural stem cell having increased passage ability, (2) a method for manufacturing a neural stem cell having said increased passage ability, (3) a method for culturing neural stem cells for increasing the passage ability of neural stem cells, (4) the use of an agent in the culturing of neural stem cells for increasing the passage ability of neural stem cells, and the like.

Means for Solving the Problems

The present inventors performed repeated investigations with non-human genetically modified animals having the N-type calcium channel gene knocked out with the aim to elucidate pathologies related to the nerve, to develop a therapy therefor, and the like.

As a result of extensive investigations to solve the above problems, we have succeeded in developing (1) a neural stem cell having increased passage ability, (2) a method for manufacturing a neural stem cell having said increased passage ability, (3) a method for culturing neural stem cells for increasing the passage ability of neural stem cells, (4) the use of an agent in the culturing of neural stem cells for increasing the passage ability of neural stem cells, and the like.

In other words, the present invention, in one aspect, relates to a neural stem cell having increased passage ability having the following characteristics:

(a) the N-type calcium channel gene is knocked out or knocked down in said cell, (b) the influx of Ca2+ via the N-type calcium channel is (1) substantially absent when the N-type calcium channel gene is knocked out, or (2) suppressed when the N-type calcium channel gene is knocked down in said cell, (c) said cell can be passaged for at least 4 generations (more preferably 15 generations) or more, and (d) said cell maintains the differentiation potential into a nerve cell even after passage for 4 generations (more preferably 15 generations).

Moreover, in one aspect of the present invention, "knockout or knockdown of the N-type calcium channel gene" in said (a) may be a knockout or knockdown that targets the gene encoding the α1B subunit of the N-type calcium channel. Moreover, in one aspect of the present invention, said "neural stem cell having increased passage ability" is shown to be nestin-positive even after passage for 4 generations (more preferably 15 generations). Moreover, in one aspect of the present invention, said "neural stem cell having increased passage ability" has high proliferation ability and high sphere-forming ability even after passage for 4 generations (more preferably 15 generations).

Moreover, the present invention, in one aspect, relates to a method for manufacturing a neural stem cell having increased passage ability, wherein said manufacturing method comprises:

(A) a step of preparing a non-human genetically modified animal having the N-type calcium channel gene knocked out or knocked down, (B) a step of isolating a neural stem cell from tissue obtained from said non-human genetically modified animal, and (C) as desired, a step of further subculturing said isolated neural stem cell, and wherein said "neural stem cell having increased passage ability" has the following characteristics:

(a) the N-type calcium channel gene is knocked out or knocked down in said cell, (b) the influx of Ca2+ via the N-type calcium channel is (1) substantially absent when the N-type calcium channel gene is knocked out, or (2) suppressed when the N-type calcium channel gene is knocked down in said cell, (c) said cell can be passaged for at least 4 generations (more preferably 15 generations) or more, and (d) said cell maintains the differentiation potential into a nerve cell even alter passage for 4 generations (more preferably 15 generations).

Here, in one aspect of the present invention, said non-human genetically modified animal may be a rodent.

Moreover, the present invention, in one aspect relates to a method for manufacturing a neural stem cell having increased passage ability, wherein said manufacturing method comprises:

(J) a step of preparing a neural stem cell in vitro, (K) a step of knocking out or knocking down the N-type calcium channel gene of said neural stem cell, and (H) as desired, a step of further subculturing said neural stem cell having the N-type calcium channel gene knocked out or knocked down, and wherein said "neural stem cell having increased passage ability" has the following characteristics:

(a) the N-type calcium channel gene is knocked out or knocked down in said cell, (b) the influx of Ca2+ via the N-type calcium channel is (1) substantially absent when the N-type calcium channel gene is knocked out, or (2) suppressed when the N-type calcium channel gene is knocked down in said cell, (c) said cell can be passaged for at least 4 generations (more preferably 15 generations) or more, and (d) said cell maintains the differentiation potential into a nerve cell even after passage for 4 generations (more preferably 15 generations).

Here, in one aspect of the present invention, the neural stem cell in said step (J) may be a cell derived from a human. Moreover, in one aspect of the present invention, the neural stem cell in said step (J) may be a neural stem cell prepared by differentiation induction of an ES or iPS cell into a neural stem cell, or may be a neural stem cell prepared as an iNS cell.

In one aspect of the present invention, in the two manufacturing methods of a neural stem cell having increased passage ability described above, said "knockout or knockdown of the N-type calcium channel gene" may be a knockout or knockdown that targets the gene encoding the α1B subunit of the N-type calcium channel.

Moreover, the present invention, in one aspect, relates to a method for culturing neural stem cells for increasing the passage ability of neural stem cells, comprising (X) a step of preparing a neural stem cell, and (Y) a step of culturing said neural stem cell under conditions that inhibit the function or expression of the N-type calcium channel.

The "culturing step" in the above step (Y) may be "a step of proliferating the neural stem cell by culturing."

Moreover, the present invention, in one aspect, in addition to the above steps (X) and (Y), may further comprise (Z) a step of evaluating that said neural stem cell cultured in said step (Y) has increased passage ability.

Further, the present invention, in one aspect, relates to a neural stem cell obtained by the above culturing method.

In one aspect of the above culturing method of the present invention, said "step of culturing under conditions that inhibit the function or expression of the N-type calcium channel" may comprise a step of applying an agent that inhibits the function or expression of the N-type calcium channel to a cell. Non-limiting examples of such an agent include ω-conotoxin GVIA and/or cyclin protein.

In one aspect of the above culturing method of the present invention, said "step of culturing under conditions that inhibit the function or expression of the N-type calcium channel" may comprise a step of applying an agent that inhibits the transcription or translation of the N-type calcium channel gene to a cell. Non-limiting examples of such an agent include shRNA or siRNA.

Moreover, the present invention, in one aspect, relates to a neural stem cell having increased passage ability having the following characteristics:

(a) the N-type calcium channel is inhibited in said cell by being cultured under conditions that inhibit the function or expression of the N-type calcium channel, (b) said cell is shown to be nestin-positive even after passage for 4 generations (more preferably 15 generations), and (c) said cell maintains the differentiation potential into a nerve cell even after passage for 4 generations (more preferably 15 generations).

Moreover, the present invention, in one aspect, relates to the use of an agent that inhibits the function or expression of the N-type calcium channel in culturing of neural stem cells for increasing the passage ability of neural stem cells. Non-limiting examples of such an agent include ω-conotoxin GVIA and/or cyclin protein.

Moreover, the present invention, in one aspect, relates to the use of an agent that inhibits the transcription or translation of the N-type calcium channel gem culturing of neural stem cells for increasing the passage ability of neural stem cells. Non-limiting examples of such an agent include shRNA or siRNA.

In this way, the present inventors have found that in regards to the neural stem cell of the present invention having increased passage ability:

- the N-type calcium channel gene is knocked out or knocked down in said cell,
- the influx of Ca2+ via the N-type calcium channel is substantially absent or suppressed in said cell,
- said cell can be passaged for at least 4 generations (more preferably 15 generations) or more,
- said cell maintains the differentiation potential into a nerve cell even after passage for 4 generations (more preferably 15 generations),
- said cell is shown to be nestin-positive even after passage for 4 generations (more preferably 15 generations), and/or
- said cell has high proliferation ability and high sphere-forming ability even after passage for 4 generations (more preferably 15 generations).

Effects of the Invention

The neural stem cell provided by the present invention has increased passage ability relative to an ordinary neural stem cell. Further, the neural stem cell provided by the present invention not only has simply increased passage ability, but maintains both "self-propagation ability" and "differentiation potential into a nerve cell."

Accordingly, by employing the neural stem cell provided by the present invention, neural stem cells or nerve cells (which are differentiated and obtained therefrom) cube easily prepared (made ready) for various experiments (such as an experiment to evaluate drug effects or side effects etc. related to an agent, and the like). Moreover, these neural stem cells or nerve cells (which are differentiated and obtained therefrom) are expected to be favorably employed for regenerative medicine.

DESCRIPTION OF EMBODIMENTS

Figure 1:
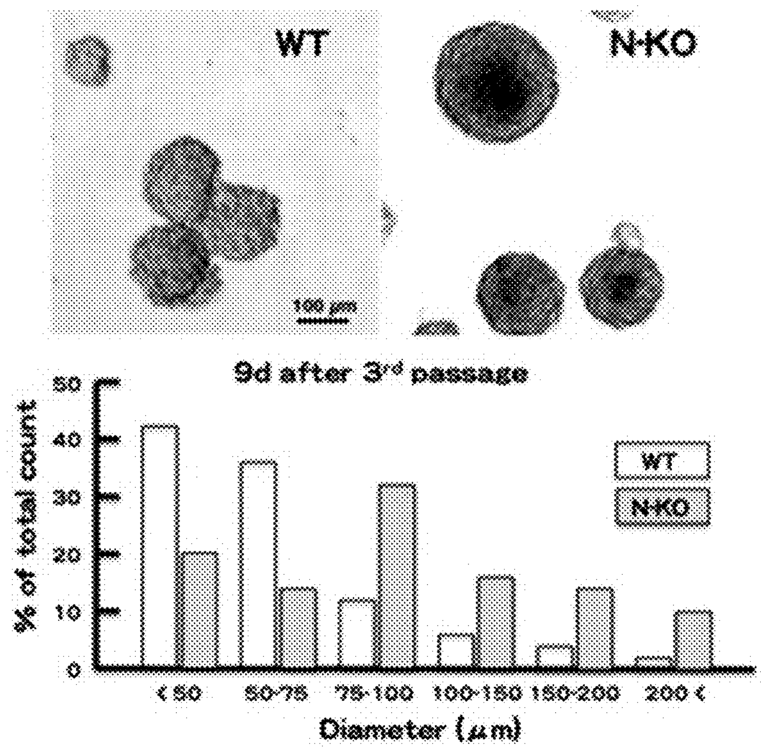
FIG. 1 shows the sphere-forming ability for each of NVDCC-deficient mouse-derived neural stem cells and WT mouse-derived neural stem cells (Example 1).

The embodiments of the present invention will be described below. The following embodiments are exemplifications to describe the present invention, and the purpose thereof is not to limit the present invention only to these embodiments. The present invention can be carried out in various embodiments.

Note that unless particularly mentioned, all technical terms, scientific terms, and specialized terms used herein have the same meanings as that generally understood by those of ordinary skill in the technical field to which the present invention belongs, and are simply employed to describe particular aspects and do not intend to be limiting. The present invention can be carried out in various embodiments as long as it does not depart from the scope thereof. All the prior art literatures, as well as published unexamined patent application publications, published examined patent applications, and other patent literatures cited herein are incorporated herein as reference, and can be employed for carrying out the present invention.

[1. Neural Stem Cell]

A neural stem cell can proliferate and repeat passaging (self-reproduction ability). A neural stem cell is also an undifferentiated cell that can create three types of cells that configure the central nervous system (i.e., nerve cells, astrocytes, and oligodendrocytes) (multipotency).

However, the neural stem cell herein is not particularly limited as long as it is a cell that may differentiate into a nerve cell. Accordingly, the neural stem cell herein is a concept that comprises a neural progenitor cell etc.

The neural stem cell employed herein can be obtained with a known method from an embryonic nerve tissue, a fetal nerve tissue, a nerve tissue of a postpartum individual, a nerve tissue of a juvenile individual, or an adult nerve tissue. The methods of U.S. Pat. Nos. 5,750,376 and 5,851,832 to Weiss et al and the like can be employed for isolating a brain tissue-derived neural stem cell.

Moreover, as another acquirement method, a neural stem cell differentiated from a stem cell such as an ES cell (Embryonic Stem cell) or an iPS cell by a known method (such as Watts C, Anatomical perspectives on adult neural stem cells. J Anat. September; 207(3):197-208. (2005)) may be employed, or a neural stem cell prepared as an iNS cell may be employed as the neural stem cell employed herein.

For example, an ES cell can be obtained with a known method such as growing a fertilized embryo, retrieving the inner cell mass (ICM) that is inside, and culturing this in a particular medium.

For example, an IPS cell can be obtained with a known method such as obtaining a cell from the skin, hair, or other tissues of an animal, introducing several particular genes into said cell with transfection or a viral vector etc., and culturing this in a particular medium.

An iNS cell (induced Neural Stem cell) herein is a cell obtained from the skin, hair, or other tissues of an animal that was directly differentiated into a neural stem cell without undergoing induction into an iPS cell. For example, an iNS cell can be obtained with a known method such as obtaining a cell from the skin, hair, or other tissues of an animal, introducing several particular genes into said cell with transfection or a viral vector etc., and culturing this in a particular medium (Stem Cells. 2012 June; 30(6):1109-1119).

The animal for supplying the neural stem cell of the present invention is not particularly limited, and examples include birds, amphibians, reptiles, fishes, mammals, and the like. A preferred aspect of the animal for supplying the neural stem cell of the present invention herein is a mammal. A mouse, a hamster, a rat, a guinea pig a rabbit, a cat, a dog, a cow, a horse, a pig, a monkey, and a human are particularly preferred, and a mouse, a rat, and a human are the most preferred as such an animal.

[2. N-Type Calcium Channel (NVDCC)]

A calcium channel (also referred to as "Ca channel") is a membrane protein that transmits information into a cell by adjusting the influx of Ca2+ into the cell.

A calcium channel may broadly comprise an ionotropic receptor, but is generally used to refer simply to a voltage-dependent calcium channel.

Various voltage-dependent calcium channels have been identified from nerve cells and muscle cells (Bean, B. P. et al, Ann. Rev. Physiol., 51:367-384, 1989, Hess P., Ann. Rev. Neurosci., 56:337, 1990). The voltage-dependent calcium channel is classified in six types of transient/low threshold activated type (T-type) and sustained/high threshold activated types (L, N, P, Q, and R-type) depending on the electrophysiological nature, sensitivity to an antagonist, and the like.

The N, P, Q, and R-type calcium channels all specifically exist in the nerve. The roles of these calcium channels in neural function are being focused (e.g. Lane D. H. et al, Science, 239:57-61, 1988, Diane L, et al, Nature 340:639-642, 1989).

Among these, the N-type calcium channel is a calcium channel characterized in that the influx of Ca2+ is suppressed by a peptide toxin w-conotoxin GVIA isolated from a cone shell. The N-type calcium channel is also referred to as NVDCC (N-Type Voltage-Dependent Calcium Channel).

The gene encoding the N-type calcium channel is referred to herein as simply the N-type calcium channel gene.

[3. Knockout and Knockdown]

The neural stem cell of the present invention having increased passage ability can also be ° Wilted by knocking out or knocking down the N-type calcium channel gene.

[3-1. Knockout (Gene Disruption)]

Knockout (sometimes referred to as gene disruption) means introducing a mutation into a gene to make the gene product thereof lose its function.

A knockout method includes targeted disruption. Targeted disruption is a method for disrupting a gene by gene targeting.

For example, targeted disruption, in regards to the base sequence of the gene to be targeted, is a method for integrating some sort of base sequence (preferably abase sequence comprising the base sequence of a selection marker gene (most typically a resistance gene for an agent)) into the base sequence of said gene to be targeted or the base sequence in the vicinity thereof so that the function of the gene product of said gene will be lost.

The gene to be targeted in the present invention is the N-type calcium channel gene. If the N-type calcium channel gene is knocked out, the gene product of the N-type calcium channel gene Will not be produced, and as an obvious result to this, the N-type calcium channel will not exert its function.

Note that targeted disruption is an exemplification of a technology to disrupt said gene based on the base sequence information of the gene encoding the N-type calcium channel. The knockout method in the present invention may be other methods as long as disruption is based on the base sequence information of said gene.

Moreover, the function of the N-type calcium channel (i.e. the gene product of the N-type calcium channel gene) in the present invention is the adjustment of Ca2+ influx. Accordingly, confirmation that the function of the N-type calcium channel is no longer exerted can be made by verifying whether or not the influx of Ca2+ that is otherwise suppressed by ω-conotoxin GVIA is substantially absent.

Here, ω-conotoxin GVIA is a peptide purified from a cone shell toxin (*Conus geographus*) (Baldomero M. O. et al., Biochemistry 23, 5087, 1984) that is characterized by the amino acid sequence set forth in SEQ ID NO. 7.

The gene encoding the α1B subunit which is a subunit of the N-type calcium channel (hereinafter sometimes referred to as "Cacna1b") cube employed as the gene encoding the N-type calcium channel to be the subject of knockout.

Specific examples of the gene encoding the α1B subunit of the N-type calcium channel can include e.g. age consisting of the following DNAs (a)-(d):

(a) a DNA consisting of the base sequences set forth in SEQ ID NOs. 1, 3, or 5.

(b) a DNA consisting of abase sequence that hybridizes to a DNA consisting of base sequences complementary to the base sequences set forth in SEQ ID NOs. 1, 3, or 5 under stringent conditions, wherein the base sequence encodes the α1B subunit of the N-type calcium channel possessing a function.

(c) a DNA consisting of base sequences encoding the amino acid sequences set forth in SEQ NOs. 2, 4, or 6.

(d) a DNA consisting of abase sequence that hybridizes to base sequences complementary to the base sequences encoding the amino acid sequences set forth in SEQ ID NOs. 2, 4, or 6 under stringent conditions, wherein the base sequence encodes the α1B subunit of the N-type calcium channel possessing a function.

The base sequence of SEQ ID NO. 1 and the amino acid sequence of SEQ ID NO. 2 are registered at GenBank as Accession Number NM000718.3, the base sequence of SEQ ID NO. 3 and the amino add sequence of SEQ ID NO. 4 are registered at GenBank as Accession Number NM001042528.1, and the base sequence of SEQ ID NO. 5 and the amino acid sequence of SEQ ID NO. 6 is registered at GenBank as Accession Number NM001195199.1.

Here, a "stringent condition" refers to a condition where only specific hybridizations occur and non-specific hybridizations do not Hybridization conditions herein can include conditions such as "2×SSC, 0.1% SDS, 50° C.," "2×SSC, 0.1% SDS, 42° C.," and "1×SSC, 0.1% SDS, 37° C.," and more stringent conditions can include e.g. "2×SSC, 0.1% SDS, 65° C.," "0.5×SSC, 0.1% SDS, 42° C.," and "0.2×SSC, 0.1% SDS, 65° C."

[3-2. Knockout (Gene Disrupted) Animal]

The knockout non-human animal for isolating the neural stem cell of the present invention is a non-human animal having the gene encoding the N-type calcium channel knocked out, and can be created according to a method for dealing a knockout non-human animal by conventional gene targeting.

The animal having the N-type calcium channel gene knocked out used herein is a non-human animal. A preferred aspect of the non-human animal having the N-type calcium channel gene knocked out used herein is a rodent A mouse is particularly preferred as such an animal.

The cloning of the N-type calcium channel α1B subunit gene, the construction of the targeting vector employed for targeted disruption, the acquisition an embryonic stem cell (ES cell) that has undergone homologous recombination, and the acquisition of a non-human knockout animal will be described below in that order with targeted disruption of the gene encoding the N-type calcium channel as the example.

1. Cloning of DNA Comprising Part of N-Type Calcium Channel α1B Subunit Gene

The DNA encoding the N-type calcium channel α1B subunit can be obtained by designing primers based on the base sequence of the DNA encoding the N-type calcium channel α1B subunit described in Thlerry C. et al, FEBS Letters, 338, 1, 1994, and performing PCR based on the genomic DNA or cDNA of a non-human animal, or by performing RT-PCR with said primers based on the RNA of a non-human animal.

As another method, the N-type calcium channel α1B subunit gene or apart thereof, preferably a clone comprising abase sequence of 500 bp or longer, and further preferably 1 kbp or longer may be selected by synthesizing a probe based on the base sequence of the DNA encoding the N-type calcium channel α1B subunit described in the abovementioned Thlerry C. et al, selecting a clone that hybridizes to said probe from the genomic DNA library or the cDNA library of a non-human animal, and determining the base sequence of the selected clone.

The restriction enzyme map of said cloned DNA can be created by confirming the restriction enzyme sites that are comprised in the base sequence of said cloned DNA.

When a DNA of sufficient length for homologous recombination, preferably a clone of 7 kbp or longer, and further preferably 10 kbp or longer could not be obtained, the DNA of sufficient length for homologous recombination may be created by cleaving out DNAs of multiple clones at appropriate restriction enzyme sites and connecting them.

2. Construction of Targeting Vector

A targeting vector herein refers to a vector employed for gene targeting, which have integrated abase sequence such that homologous recombination of DNA occurs when it is contacted with the gene to be targeted.

The DNA employed for homologous recombination can be obtained by introducing a positive selection marker such as a drug resistance gene, preferably a neomycin resistance gene into the restriction enzyme site of the exon region in the DNA of sufficient length for homologous recombination obtained by said cloning. Moreover, a portion of the exon may be removed from said DNA employed for homologous recombination to substitute with a drug resistance gene instead. When there are no appropriate restriction enzyme sites in the base sequence of the DNA obtained by said cloning, an appropriate restriction enzyme site may be introduced and this restriction enzyme site may be employed to introduce a drug resistance gene etc. into the DNA employed for homologous recombination by PCR employing primers designed to comprise a restriction enzyme site, by ligation of an oligonucleotide comprising a restriction enzyme site, and the like.

The targeting vector herein preferably comprises a negative selection marker such as a thymidine kinase gene and a diphtheria toxin gene etc. in order to remove ES cells in which no homologous recombination occurs between the DNA on the targeting vector introduced into a cell and the N-type calcium channel α1B subunit gene of the ES cell having the targeting vector introduced, but instead, the DNA on the introduced targeting vector was inserted into a site other than the N-type calcium channel α1B subunit gene.

These recombinant DNA technologies can be performed by the method described in e.g. Sambruck, J., Fritsch, E. F., and Maniatis, T. (1989) Molecular Cloning: A Laboratory Manual, Cold Spring Harbor Laboratory, Cold Spring Harbor, N.Y., but it is not limited thereto as long as an appropriate recombinant DNA can be obtained.

3. Acquisition of Embryonic Stem Cells (ES Cells) that have Undergone Homologous Recombination The created said targeting vector is made into a linear DNA by dealing with a restriction enzyme, and purified by a method such as phenol/chloroform extraction, agarose electrophoresis, ultracentrifugation, and the like. The purified said linear DNA is then transfected to an ES cell such as TT2. Examples of the transfection method can include electroporation, lipofection, and the like, but the transfection method herein is not limited to these methods.

An ES cell having the targeting vector transfected is cultured in an appropriate selection medium (for example, in a selection medium comprising neomycin and ganciclovir in the medium when a targeting vector that have integrated a neomycin resistance gene and a thymidine kinase gene was constructed).

The confirmation that appropriate homologous recombination is occurring to the DNA of said ES cell that have proliferated with drug resistance in the selection medium, can be made e.g. by a method as follows.

(i) Integration of a neomycin resistance gene and a thymidine kinase gene (these genes are sometimes referred to herein as "transgenes") can be cagily confirmed by PCR etc. (ii) Further, whether or not homologous recombination has occurred can be confirmed by performing Southern blot analysis of the DNA of said ES cell using apart of the DNA 5' upstream or 3' downstream on the outside of the targeting vector as the probe. (iii) Moreover, confirmation that the targeting vector is not inserted into any portion other than the target gene site can be made by performing Southern blot analysis using the DNA inside the targeting vector as the probe. ES cells that have undergone homologous recombination can be acquired by combining these methods.

The method of introducing a mutation into a target gene by introducing age inserted so that the function of the gene product will be lost into an embryonic stem cell, and selecting an embryonic stem cell that has undergone homologous recombination between the introduced gene and the target gene, can also be performed by the method described in e.g. Suzanne L. et. al., Nature, 336, 348, 1988.

4. Method for Creating Non-Human Knockout Animal

A preferred aspect of a non-human animal having the N-type calcium channel gene knocked out that can be used herein is a rodent. A mouse is the most preferred as such an animal.

The method for creating a non-human knockout animal will be described below with a mouse as an example.

A knockout mouse is created via the following steps: the collection of 8-cell stage embryos after fertilization or blastocysts, the microinjection of ES cells Cat have undergone homologous recombination, the transplantation of engineered eggs into a pseudopregnant mouse, the parturition of the pseudopregnant mouse and nursing of litters, the selection of the transgenetic mice by PCR and Southern blot methods, and the establishment of a mouse lineage possessing a transgene (Yogi T. et. al., Analytical Biochem. 214, 70, 1993).

(1) Collection of 8-Cell Stage Embryos or Blastocysts

Eight-cell stage embryos are obtained by intraperitoneally administering each of 5 international units of pregnant mare serum gonadotropin and 2.5 international units of human chorionic gonadotropin to a female mouse in order to induce superovulation, and then mating with a male mouse, resecting the fallopian tube and the uterus from the female mouse at 2.5 days after mating, and then perfusing. When blastocysts are employed, the embryos are obtained by resecting the uterus of the female mouse at 3.5 days after mating and then perfusing.

(2) Microinjection of ES Cells that have Undergone Homologous Recombination

ES cells Cat have undergone homologous recombination acquired by the method described in said "3. Acquisition of Embryonic Stem Cells (ES Cells) that have Undergone Homologous Recombination" are microinjected into the 8-cell stage embryos or blastocysts obtained in (1). Microinjection can be performed, for example, based on the method described in Hogan, B. L. M., A laboratory Manual, Cold Spring Harbor Laboratory Press, Cold Spring Harbor, N.Y., 1986, Yagi T. et al., Analytical Biochem 214, 70, 1993, under an inverted microscope, with a micromanipulator, a microinjector, an injection pipette, and a holding pipette. Moreover, a droplet of 5 μl of the medium and a droplet of suspended ES cells created on Falcon 3002 (Becton Dickinson Labware) layered with liquid paraffin can be employed as the dish for injection.

The 8-cell stage embryo or blastocyst microinjected with an ES cell that has undergone homologous recombination herein is referred to as an "engineered egg."

(3) Transplantation of Engineered Eggs into Pseudopregnant Mouse

A pseudopregnant mouse is created by mating a vasoligated male mouse and a wildtype female mouse, and once it is in a pseudopregnant state, the engineered eggs created in (2) are transplanted.

The transplantation fiction of the engineered eggs can be performed based on the methods described in e.g. Hogan, B. L. M., A laboratory Manual, Cold Spring Harbor Laboratory Press, Cold Spring Harbor, N.Y., 1986 or Yagi T. et al., Analytical Biochem 214, 70, 1993.

An example of specific operation will be described below, but the transplantation of engineered eggs herein is not limited thereto.

A pseudopregnant mouse is subjected to general anesthesia with e.g. 50 mg/kg body weight of pentobarbital sodium, about 1 cm of both flanks are incised to expose the ovary and the fallopian tube, and the vursa ovarica is incised under a stereomicroscope with tweezers to expose the fimbria of fallopian tube. Next, the engineered eggs are delivered from the fimbria of fallopian tube at a rate of 7 to 8 eggs per fallopian tube. At this time, the confirmation of transplantation inside the fallopian tube can be made by visually observing microbubbles inserted together with the engineered egg under a stereomicroscope.

The fallopian tube and the ovary of the mouse having transplanted the engineered eggs are returned to the peritoneal cavity, both incision sites are sutured, and then aroused from anesthesia.

In some cases, the engineered eggs may be cultured until the day after creation and developed to a blastocyst stage before transplanting to the uterus of a pseudopregnant mouse.

(4) Parturition of Pseudopregnant Mouse and Nursing of Litters

In many cases the baby nice can be obtained by day 17 after the transplantation of engineered eggs. The baby mice are ordinarily chimeras of a cell derived from an ES cell that has undergone homologous recombination and a cell derived from the mouse from which the fertilized egg was collected. For example, when TT2 was employed as an ES cell, and TT2 that has undergone homologous recombination was injected into the 8-cell stage embryo collected from an ICR mouse, the body hair color baby nice with high chimerism became dominant agouti, and the body hair color of mice with low chimerism became dominant white.

(5) Selection of Transgenetic Mouse by PCR and Southern Blot Methods

The confirmation of whether the transgene is inserted into the germ cell of said chimeric mouse can be made e.g. by a method as follows.

(i) When said chimeric mouse was mated with a mouse having white body hair color (such as ICR), the presence or absence of the transgene can be easily confirmed by verifying the body hair color of the baby mouse obtained (ii) The presence or absence of the transgene can also be confirmed by extracting DNA from the tail of the baby mouse obtained and subjecting it to PCR. (iii) Moreover, a more authentic genotypic identification can be performed by performing Southern blot analysis instead of PCR.

Here, since a chimeric mouse with high chimerism is expected to comprise the transgene in the germ cell as well, it is preferred to subject a mouse with chimerism that is as high as possible for mating.

(6) Establishment of Mouse Lineage Possessing Transgene

An N-type calcium channel knockout mouse where the transgene exists in homo (sometimes referred to herein as an "N-KO mouse" or an "NVDCC-deficient mouse") can be obtained by mating hetero N-type calcium channel knockout nice (sometimes referred to herein as an "He mouse") with each other. The N-KO mouse can be obtained by any of mating He mice with each other, an He mouse and an N-KO mouse, and N-KO nice with each other.

A neural stem cell having the N-type calcium channel knocked out can be obtained from an embryonic nerve tissue, a fetal nerve tissue, a nerve tissue of a postpartum individual, a nerve tissue of a juvenile individual, or an adult nerve tissue of the knockout animal obtained as such with a preparation method described below.

[3-3. Knockdown]

Knockdown herein refers to decreasing the amount of transcription or inhibiting the translation of a particular gene by transformation. In other words, it refers to those that do not completely extinguish gene function, but decrease (attenuate) the targeted gene function.

The antisense method which is introducing an RNA corresponding to the antisense chain of mRNA into a cell cube employed as the method for knocking down age. RNAi (RNA interference) which employs a double-stranded RNA (shRNA, siRNA) or a microRNA etc. can also be utilized as the method for knocking down age.

More specifically, a method for decreasing the amount of transcription or inhibiting the translation of a particular gene by transforming a cell with an shRNA or siRNA expression vector or by transforming a cell with an siRNA can be employed as the method for knocking down age.

In mammalian cells, it is known that expression of only a single mRNA or protein is specifically suppressed with RNA interference by a short RNA of 30 bp or less.

[3-4. Knockdown Animal]

A knockdown animal is an animal in which a short double-stranded RNA (shRNA, siRNA) or an antisense nucleic acid corresponding to the mRNA of the target gene is artificially introduced and expressed in a cell configuring said animal to suppress the expression of the target gene by the action of said siRNA or antisense nucleic acid. Such a knockdown animal can be created by employing e.g. an siRNA expression system by a vector system (e.g. Science 296:550-553 (2002), Nature Biotech. 20:500-505(2002)).

Note that an animal having the N-type calcium channel gene knocked down that can be used herein is a non-human animal. A rodent is particularly preferred, and a mouse is the most preferred as such an animal.

An example of a method for creating an animal having the N-type calcium channel knocked down is described below. In the example shown below, the gene encoding the N-type calcium channel to be the subject of knockdown is the gene encoding the α1B subunit which is a subunit of the N-type calcium channel.

The siRNA, shRNA etc. for inhibiting the N-type calcium channel gene is not particularly limited as long as it is a nucleic acid that can inhibit the transcription or translation of the N-type calcium channel gene, and those skilled in the art will be able to appropriately design and manufacture the sequence of the siRNA, shRNA etc.

A vector that expresses an shRNA that inhibits the transcription or translation of the N-type calcium channel gene can be designed so that the sequence of the region encoding shRNA has e.g. the following characteristics of comprising:

(i): a sequence of 11 to 30 contiguous bases (preferably 21 to 25 bases) in the base sequence encoding the N-type calcium channel gene, (ii): abase sequence complementary to the sequence of (i) and in reverse orientation, and (iii): abase sequence that links the base sequence of (i) and the base sequence of (ii), and when regions (i)-(m) are transcripted into an RNA, the RNA portion transcripted from (i) and the RNA portion transcripted from (ii) font b a double-stranded RNA, and the RNA portion transcripted from (iii) forms a loop region that links the said double-stranded RNA.

The above shRNA expression vector preferably further comprises a polymerase II-based promoter or a developmental process-specific promoter, and an example of such a promoter can include the cytomegalovirus (CMV) early gene promoter.

Moreover, the above shRNA expression vector preferably further comprises a sequence that autocatalytically cleaves the RNA such as a ribozyme site etc. upstream of the base sequence of said regions (i)-(iii).

The above shRNA expression vector preferably further comprises a sequence that stops the RNA polymerase such as a MAZ domain sequence etc. downstream of the base sequence of said regions (i)-(iii).

Moreover, the base sequence of (iii) in the above shRNA expression vector is not particularly limited as long as it can take an appropriate loop structure.

An N-type calcium channel non-human knockdown animal can be created by employing e.g. a method similar to the method described in "3-2. Knockout (Gene Disrupted) Animal" herein. In this use, an N-type calcium channel non-human knockdown animal can be created by employing an shRNA expression vector instead of the targeting vector employed in the method described in "3-2. Knockout (Gene Disrupted) Animal."

A neural stem cell having the N-type calcium channel knocked down can be obtained from an embryonic nerve tissue, a fetal nerve tissue, a nerve tissue of a postpartum individual, a nerve tissue of a juvenile individual, or an adult nerve tissue of the non-human knockdown animal obtained as such with a preparation method described below.

[4. Agent that Inhibits Function or Expression of N-Type Calcium Channel]

An agent that inhibits the function or expression of the N-type calcium channel that can be used herein is not particularly limited as long as it transiently inhibits or decreases (attenuates) the N-type calcium channel of the neural stem cell, examples of which can include a chemical substance, a protein, age, and the like. More specifically, ω-conotoxin GVIA, cyclin protein, and the like can be included.

An agent that inhibits the function or expression of the N-type calcium channel herein also includes an agent that inhibits the transcription or translation of the N-type calcium channel gene. More specifically, a chemically synthesized siRNA, an siRNA transcripted in vitro using an enzyme, an siRNA mix produced by cleaving a dsRNA with Dicer or RNase III, an siRNA expression cassette synthesized by PCR, and the like can be included.

The inhibition of the N-type calcium channel of the neural stem cell with these agents that inhibit the function or expression of the N-type calcium channel can be achieved by adding said agent that inhibits the function or expression of the N-type calcium channel to the neural stem cell under an appropriate temperature in an appropriate medium such as DMEM/F12 (DMEM/Ham's F-12).

[5. Preparation of Neural Stem Cell]

The neural stem cell of the present invention can be prepared e.g. by a method shown below.

[5-1. Preparation of Non-Human Knockout or Knockdown Animal-Derived Neural Stem Cell]

The brain, preferably the cerebrum, the hippocampus, and the lateral ventricle etc. of a non-human animal having the N-type calcium channel gene knocked out or knocked down by the method described in [3. Knockout and Knockdown] herein were resected by conventional means, loosened in an appropriate medium such as DMEM/F12 (DMEM/Ham's F-12) medium to prepare a single cell suspension. Said single cell suspension is subsequently filtrated with e.g. a nylon mesh, and then the tissue is subjected to several minutes of centrifugation at e.g. about 100 to 300 g, and collected as a precipitate. Next, the cells collected as said precipitate are resuspended in an appropriate medium such as DMEM/F12 (DMEM/Ham's F-12) medium. Said resuspended cells are further centrifuged, the precipitate is collected, and the resuspension operation is repeated several times to wash the cells. Next, said washed cells are suspended in an appropriate medium such as DMEM/F12 (DMEM/Ham's F-12) medium comprising a growth factor such as EGF or FGF, a serum replacement supplement such as N2 supplement, as well as an antibiotic such as penicillin G, streptomycin, and amphotericin B as necessary.

When cells suspended in said medium are cultured, some cells start to proliferate and start to form spheres (cell masses). Spheres (cell masses) cube obtained in about two weeks by continuing further culturing with medium exchange at a rate of several times a week.

[5-2. Preparation of Neural Stem Cell Obtained from Genetically Unmodified Animal-Derived Neural Stem Cell by Knocking Out N-Type Calcium Channel Gene]

A genetically unmodified animal-derived neural stem cell can be prepared by a method similar to the method described in [5-1. Preparation of Non-human Knockout or Knockdown Animal-derived Neural Stem Cell] herein from a genetically unmodified animal-derived tissue.

Further, by knocking out the N-type calcium channel gene of the genetically unmodified animal-derived neural stem cell prepared as above with a technology such as zinc finger nuclease or TALEN, a desired neural stem cell can be obtained. Moreover, by knocking out the N-type calcium channel gene with a known method at the ES or iPS cell stage, and performing differentiation induction with e.g. the method described in [8. differentiation potential] below, a desired neural stem cell cube obtained.

[5-3. Preparation of Neural Stem Cell Obtained from Genetically Unmodified Animal-Derived Neural Stem Cell by Knocking Down N-Type Calcium Channel Gene]

A genetically unmodified animal-derived neural stem cell can be prepared by a method similar to the method described in [5-1. Preparation of Non-human Knockout or Knockdown Animal-derived Neural Skin Cell] herein from a genetically unmodified animal-derived tissue.

Further, by knocking down the N-type calcium channel gene of the genetically unmodified animal-derived neural stem cell prepared as above with an shRNA expression vector or an siRNA expression vector, or by transforming the cell with an siRNA, a desired neural stem cell can be obtained.

A hairpin-type RNA expression vector or a la idem-type RNA expression vector can be employed as said shRNA or siRNA expression vector. A hairpin-type RNA vector is an expression vector having the base sequence of shRNA inserted downstream of the promoter sequence, and the shRNA transcripted from the introduced expression vector is transported from the nucleus to the cytoplasm and receives processing by Dicer to become a double-stranded siRNA similar to siRNA. A tandem-type RNA vector is a vector having the template sequences of sense and antisense chains each having a promoter sequence inserted, and sense and antisense chains which are each separately transcripted anneal to form an siRNA.

[5-4. Preparation of Neural Stem Cell by Addition of Agent that Inhibits Function or Expression of N-Type Calcium Channel to Genetically Unmodified Animal-Derived Neural Stem Cell]

A genetically unmodified animal-derived neural stem cell can be prepared by a method similar to the method described in [5-1. Preparation of Non-human Knockout or Knockdown Animal-derived Neural Skin Cell] herein from a genetically unmodified animal-derived tissue.

A genetically unmodified animal-derived neural stem cell can also be prepared as follows. Neural stem cells differentiation induced from a genetically unmodified ES or iPS cell with e.g. the method described in [8. differentiation potential] below are obtained, or neural stem cells prepared as iNS cells differentiation induced from genetically unmodified animal-derived cells are obtained, and collected on a dish while adding a medium such as Bullet Kit as necessary. Next, the neurospheres formed from neural stem cells are collected by centrifugal separation. The desired cells can be obtained by culturing said neurospheres in a medium such as Bullet Kit medium comprising an N-type calcium channel inhibitor such as ω-conotoxin GVIA and cyclin protein. Further, in said culturing method, the medium may be exchanged several times a week as necessary, and cells may be passaged once in several days as necessary.

The genetically unmodified animal-derived neural stem cells, or the neural stem cells differentiation induced from genetically unmodified ES or iPS cells, or the iNS cells differentiation induced from genetically unmodified animal-derived cells may be frozen as necessary and thawed before use.

In contrast to neural stem cells prepared as above, the desired cells can be obtained by inhibiting the function or expression of the N-type calcium channel e.g. with a method as follows.

(1) Method for Applying Substance that Inhibits Function or Expression of N-Type Calcium Channel to Cell Neural stem cells suspended in a medium are seeded in a flask, FGF-b and EGF are added as necessary, and an agent such as w-conotoxin GVIA and cyclin protein are further added and cultured. Moreover, half of the medium may be exchanged every several days as necessary.

(2) Method for Introducing Chemically Synthesized ShRNA or SiRNA into Cell

SiRNA which is chemically synthesized two RNAs (sense and antisense chains) that are annealed is chemically synthesized or purchased from e.g. Dharmacon, Inc., shRNA is purchased from e.g. Dharmacon, Inc., and introduced into a neural stem cell with a known method such as transfection, microinjection, and electroporation. The introduced shRNA or siRNA inhibit the expression of the N-type calcium channel by forming RISC in the cytoplasm and causing target gene mRNA sequence-specific degradation.

(3) Method for Introducing SiRNA Transcripted In Vitro Using Enzyme into Cell

An siRNA is synthesized from a template sequence combined with a promoter (T7, T3, SP6) used in in vitro transcription, using an RNA polymerase. After the synthesized siRNA is purified, this is introduced into a neural stem cell with a known method such as transfection, microinjection, and electroporation in order to inhibit the function or expression of the N-type calcium channel.

(4) Method for Introducing SiRNA Mix Produced by Cleaving DsRNA with Dicer or RNase III into Cell The function or expression of the N-type calcium channel is inhibited by introducing a fragment (siRNA) mix of along-chain dsRNA cleaved with Dicer or RNase III into a neural stem cell with a known method such as transfection, microinjection, and electroporation Since siRNA corresponding to the base sequences of various portions of the target gene are admixed in the RNA fragment to be introduced, the probability of being able to knock down the target gene can be enhanced.

(5) Method for Introducing SiRNA Expression Cassette Synthesized by PCR into Cell The function or expression of the N-type calcium channel is inhibited by introducing a PCR product composed of the sequence promoter-shRNA template sequence-transcription termination signal into a neural stem cell with a known method such as transfection, microinjection, and electroporation.

[6. Culturing of Neural Stem Cells]

The method for culturing neural stem cells is not particularly limited as long as it is a culturing method where said cells can survive, proliferate, or differentiate into nerve cells, but the neurosphere method is preferred.

The neurosphere method that can be used herein is one of the generally used selective culturing methods for neural stem cells. The neurosphere method is a method of suspension culturing neural stem cells under an appropriate temperature condition with a serum-free medium comprising EGF and/or bFGF in order to allow proliferation of neural stem cells as spherical cell masses (neurospheres).

Human neural stem cells, similarly to rodent neural stem cells, can be maintained in a serum-free culture medium comprising a mitogen (representatives are epithelium proliferative factor and/or basic fibroblast proliferative factor). Said neural stem cells suspended in a medium proliferate and form cell aggregates known as cell masses (neurospheres).

[7. Subculture]

The neural stem cells of the present invention can be passaged by a known method. Passaging refers to transferring a portion of cells to anew medium and culturing it as a next generation. Passaging of neural stem cells by an ordinary neurosphere method is about 3 passages. The neural stem cells obtained by the present invention are neural stem cells that can be passaged for 4 passages or more, preferably 5 passages or more, more preferably 6 passages or more, further preferably 7 passages or more, inter alia preferably 8 passages or more, particularly preferably 9 passages or more, and most preferably 10 passages or more, but said number of passages is not particularly limited as long as the differentiation potential to differentiate into nerve cells is retained.

Moreover, the substrate for subculturing the neural stem cells is not particularly limited as long as it is a substrate that allows normal passaging without promoting differentiation/induction of the neural stem cells. Said substrate preferably consists of e.g. a ceramic or a glass of at least any one of zirconia, yttria, titania, alumina, silica, hydroxyapatite, and β-tricalcium phosphate.

These ceramics or glass can be favorably employed because they have high biostability without promoting differentiation/induction of undifferentiated cells.

In the subculturing method of neural stem cells used herein, cell masses of neural stem cells that were proliferated while still in an undifferentiated state cube obtained by employing a culturing substrate as described above, and seeding and culturing said neural stem cells at at least one position in said culturing substrate.

Further, in said subculturing method, subculture can be performed by dispersing cell masses cultured and obtained as above into single cells or cell subpopulations, aid repeating the above culturing method with the neural stem cells obtained. Moreover, separation of the cell mass can be easily performed by treating the cell mass with e.g. papain or trypsin, or by pipetting the cell mass.

[8. Differentiation Potential]

Differentiation potential refers to the ability of a cell to differentiate into a different cell type. Neurodifferentiation potential herein refers to the ability to differentiate into a nerve cell. Examples of a cell having the ability to differentiate into a nerve cell herein can include a neural stem cell, a neural progenitor cell, and the like. A cell having the ability to differentiate into a nerve cell also comprises a neural stem cell, a neural progenitor cell, and the like that are differentiation induced from a stem cell such as an ES or iPS cell with a known method. Further, a cell having the ability to differentiate into a nerve cell also comprises a neural stem cell prepared as an iNS cell, a neural progenitor cell that is differentiation induced from said cell, and the like.

Differentiate from an ES cell into a neural stem cell can be performed e.g. by a method as follows.

First, ES cells prepared with the method as above are cultured under a condition without feeder cells or LIF. Next, said cultured ES cells were suspended once by enzyme treatment or mechanical detachment, and separated into small masses by pipetting. In addition, by further culturing said separated ES cell small masses in a new culture dish, ES cells spontaneously differentiate via embryoids into neural stem cells (Roy. S. et al., Mol. Cell. Biol., 18:3947-3955 (1998)).

These embryoids can be obtained by culturing ES cells in an uncoated culture dish with an ES cell medium without LIF for about 7 to 14 days and observing the appearance of spheres that are formed by aggregation of cells under a microscope. These embryoids can also be obtained by culturing in the presence of vitamin B12 as necessary and heparin or a substance with heparin-like action (Republication of Published Examined Patent Application 2006-004149).

For example, those prepared by a method known to those skilled in the art (Doetschman T C, et al. J Embryol Exp Morphol, 1985, 87, 27-45, Williams R L et al., Nature, 1988, 336, 684-687) can also be employed as ES cells.

A neural stem cell differentiated from a stem cell such as an iPS cell cube obtained with a method similar to said method for differentiating an ES cell into a neural stem cell.

Those prepared by a known method (Stem Cells. 2012 June; 30(6):1109-1119) can also be employed as neural stem cells prepared as iNS cells.

[9. Differentiation from Neural Stem Cell into Nerve Cell]

The neural stem cell of the present invention can be differentiated into a nerve cell by a known method Specifically, the neural stem cells of the present invention are cultured e.g. in a medium such as Dulbecco's modified Eagle's medium/Nutrient mixture F-12 Ham medium, with addition of a growth factor etc. such as EGF and FGF as necessary. The neural stem cells of the present invention are cultured preferably in the form of neurospheres. The neural stem cells of the present invention are cultured while exchanging about half of the medium about several times a week as necessary.

The neurospheres are dispersed into individual cells with an enzyme such as NeuroCult after 5 to 100 passages, preferably 10 to 70 passages, and further preferably 30 to 50 passages. Next, the neural stem cells dispersed into individual cells are seeded at a cell density of $1\times10^3$ to $1\times10^6$, preferably $1\times10^4$ to $5\times10^5$ on a Cellware. The seeded cells are cultured in a medium without a proliferative factor under an appropriate temperature condition in the presence of a few % of carbon dioxide as necessary for several weeks to allow differentiate into nerve cells.

Moreover, the neural stem cells of the present invention are also differentiation induced by seeding on a multi-electrode culture dish coated in advance with e.g. poly-D-lysine, and culturing under an appropriate temperature condition in the presence of a few % of carbon dioxide as necessary for a several weeks. During the differentiation step, said neural stem cells are maintained in a medium without a proliferative factor.

The neural stem cells of the present invention can be differentiated into nerve cells by the above steps. Half of the medium may be exchanged about several times per week as necessary.

[10. Culturing Condition]

The cell culturing temperature condition of the present invention is 20° C. to 40° C., preferably 33 to 39° C., further preferably 36 to 38° C., and most preferably 37° C.

Other culturing conditions are not particularly limited as long as it is a condition that cells can be appropriately grown. Cells may be cultured in a suspended state (Neurosphere state) or may be cultured adhered to the culture vessel.

[11. Evaluation of Agents]

Evaluation of agents employing the neural stem cells of the present invention can be performed by for example adding an agent to neural stem cells or nerve cells differentiated from neural stem cells, and investigating the change in action potential of said cells before and after adding the agent or the morphological change of cells.

Specifically, evaluation can be performed by the method exemplified below.

Said nerve cells on an electrode culture dish are left standing in an incubator under an appropriate temperature condition during measurement of action potential. Electric field potential that occurred at probes at 64 locations are all recorded with a measuring device such as a multi-channel recording system at a sampling speed of several to several tens of kHz, and at the same time filtered with a several tens to hundreds of Hz passband filter. The baseline threshold of electric potential by spontaneous activity of the neurons was measured for each experiment, and the change in average frequency can be recorded after adding the agent to be the subject of evaluation.

Said baseline threshold can be adjusted according to the agent, and for example can be set at ±0.001 to 0.020V in an 4-aminopyridine (4-AP) activation experiment, and at −0.001 to 0.010 mV in a tetradotoxin (TTX) suppression experiment Spike frequency (Hz) exceeding the threshold cube averaged as necessary. Baseline activity and activity after stimulation were each measured for several hundred seconds for the activation experiment of each agent.

The measurement of action potential of cells can also be performed by fixing the neural stem cells of the present invention with a manipulator or a micromanipulator etc., directly inserting an injection pipette etc. into said neural stem cells or nerve cells differentiated from said neural stem cells, and measuring the intracellular electric potential.

Evaluation of an agent (e.g. the influence of the agent on neural stem cells or nerve cells (regardless of main effect or side effect)) can be performed without directly administering said agent to a human by investigating the action potential of the neural stem cells of the present invention or nerve cells differentiated from said neural stem cells before and after addition of the agent.

[12. Regenerative Medicine]

Humans sometimes suffer a deficient state, dysfunction, or dysfunction of cells, tissues, and organs etc. of the body due to accidents or illnesses etc. Regenerative medicine is a medical care to rebuild the function of said cells, tissues, and organs etc. by transplanting cells, tissues, and organs etc. to the body in order to regenerate the lost function of cells, tissues, and organs etc.

The neural stem cells of the present invention can be appropriately proliferated as necessary, and can further be cultured so that they differentiate into nerve cells. For this reason, the neural stem cell of the present invention may become a material of regenerative medicine for neurological diseases including spinal cord damage, Parkinson's disease, and the like. In other words, the present invention can provide a neural stem cell for regenerative medicine, and a nerve cell differentiated from said neural stem cell.

EXAMPLES

The present invention will now be specifically described by Examples below, but the present invention is not to be limited in any way by these Examples.

Example 1

Establishment of N-Type Calcium Channel Knockout (NVDCC-Deficient) Mouse-Derived Neural Stem Cells, and Analysis of Proliferation Ability and Differentiation Potential into Nerve Cells 1. Establishment of NVDCC-Deficient Mouse-Derived Neural Stem Cells Preparation of neural stem cells was performed by the following method.

First, the surrounding tissue of the lateral ventricle of 10-week old male NVDCC-deficient nice (C57BL6N) was resected by conventional means. The resected cell tissues were then dispersed with Neural Tissue Dissociation Kit (papain), and separated into neural stem cells with Anti-Prominin-1 microbeads (Catalog #130-092-752 from Miltenyi Biotec GmbH).

Cells obtained as above were suspended in D-MEM/Ham's F-12 (1:1) medium (Catalog #11039-021, from Invitrogen Corporation) comprising ×1 B-27™ Supplement (Catalog #12587010, from GIBCO Inc.), ×1 N2-Supplement (Catalog #17502-048, from Invitrogen Corporation), and ×1 Penicillin-Streptomycin mixed solution (Catalog #P4333, from Sigma-Aldrich Corporation), seeded in a 25 $cm^2$ flask (Catalog #3103-025X, from IWAKI), and FGF (fibroblast growth factor)-b (Catalog #450-33, from peprotech) and EGF (epidermal growth factor) (Catalog #PGM8045, from invitrogen Corporation) at final concentrations of 25 ng/ml were added.

The day of culture initiation was set as day 0, FGF-b and EGF were incrementally added on days 3 and 6, neurospheres were collected/dispersed on days 9 to 10, seeded under environmental conditions similar to the above, and this was employed as the passage. Note that when passaging, a medium of the medium employed for culture before said passaging and the newly employed medium mixed at 1:1 was employed.

Moreover, as a control experiment, neural stem cells were prepared/passaged from the surrounding tissue of the lateral ventricle of a 10-week old male wildtype (WT) mouse (C57BL6N) with a similar method.

As used herein, neural stem cells at the time of acquisition from a tissue are referred to as passage 0 neural stem cells. In other words, neural stem cells acquired from a tissue that were passaged once are referred to as neural stem cells after the 1st passage.

2. Observation of Sphere Formation and Proliferation Ability of NVDCC-Deficient Mouse-Derived Neural Stem Cells The sphere-forming ability of NVDCC-deficient mouse-derived neural stem cells and WT mouse-derived neural stem cells after the 1st passage was 28 spheres/mouse and 6.2 spheres/mouse, respectively (average value of three trials). In other words, NVDCC-deficient mouse-derived neural stem cells showed a higher value than WT mouse-derived neural stem cells.

Moreover, NVDCC-deficient mouse-derived neural stem cell and WT mouse-derived neural stem cell neurosphere images (photographs) on day 9 after the 3rd passage, as well as the histogram of the measurement results of the diameter of each neurosphere are shown in FIG. 1.

Figure 2:
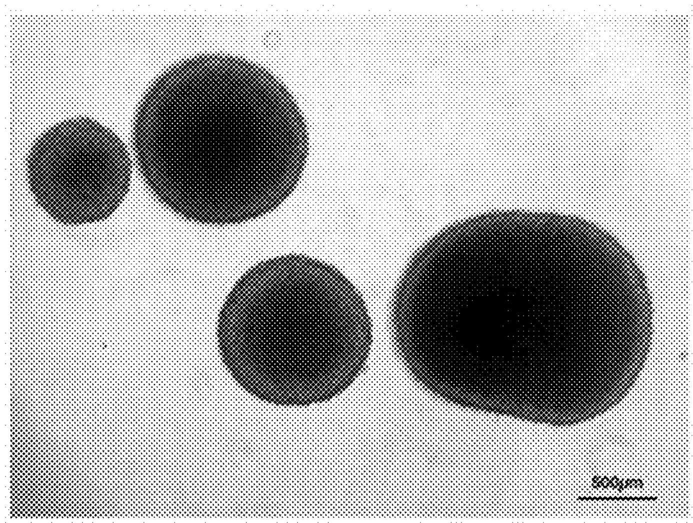
FIG. 2 shows that NVDCC-deficient mouse-derived neural stem cell neurospheres have proliferation ability even after repeated passages (Example 1).

NVDCC-deficient mouse-derived neural stem cell neurospheres showed a large and healthy aspect compared to WT mouse-derived neural stem cell neurospheres. In fact, thereafter, after the 4th passage WT mouse-derived neural stem cells neither formed neurospheres nor proliferated and lead to cell death. On the other hand, NVDCC-deficient mouse-derived neural stem cells could form neurospheres thereafter, and were able to repeat passaging with good proliferation ability. In fact, its proliferation ability was stabilized after every passage, leading to the formation of massive spheres by the 5th passage. The massive neurosphere image (photograph) is shown in FIG. 2.

3. Differentiation Potential of NVDCC-Deficient Mouse-Derived Neural Stem Cells into Nerve Cells In general, it is known that neural stem cells, with repeated passaging, (1) decrease its self-propagation ability, as well as (2) lose its differentiation potential into nerve cells and tend to differentiate into glial cell. However, NVDCC-deficient mouse-derived neural stem cells could repeat passaging (1) without decreasing its self-propagation ability, and (2) without losing its differentiation potential into nerve cells.

For example, NVDCC-deficient mouse-derived neural stem cell neurospheres after the 15th passage are positive fornestin (class intermediate filament protein) which is a multipotent neural stem cell marker. This means that said neural stem cells retain multipotency even after the 15th passage.

Figure 3:
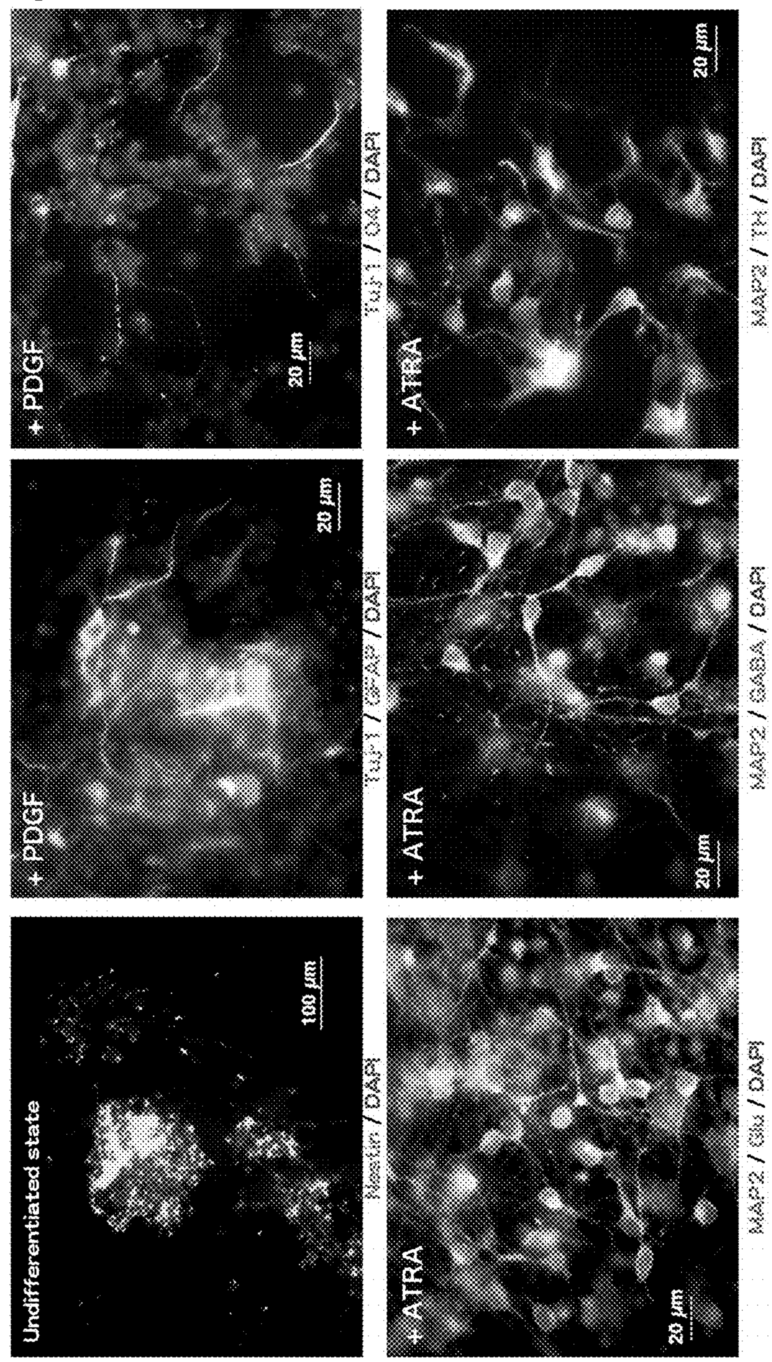
FIG. 3 shows the differentiation from neural stem cells into various types of nerves (Example 1).

When 5 days of differentiation induction was performed on said neural stem cells with 10 ng/ml of PDGF (platelet-derived growth factor)-AA differentiation into (1) Tuj1 (class β-tubulin)-positive nerve cells, (2) GFAP (grail fibrillary acidic protein)-positive astrocytes, and (3) O4 (sulfatide antigen)-positive oligodendrocyte could be confirmed (FIG. 3).

Moreover, when 5 days of differentiation induction was performed on said neural stem cells with 100 ng/ml of ATRA (all-trans retinoic acid), most cells differentiated into MAP2 (microtubule-associated protein 2)-positive nerve cells, and terminal differentiation into various types of nerve cells (such as glutamic acid-positive nerve cells, GABA (γ-aminobutyric acid)-positive nerve cells, TH (tyrosine hydroxylase: dopamine-containing neural marker)-positive nerve cells etc.) was also confirmed (FIG. 3).

Figure 4:
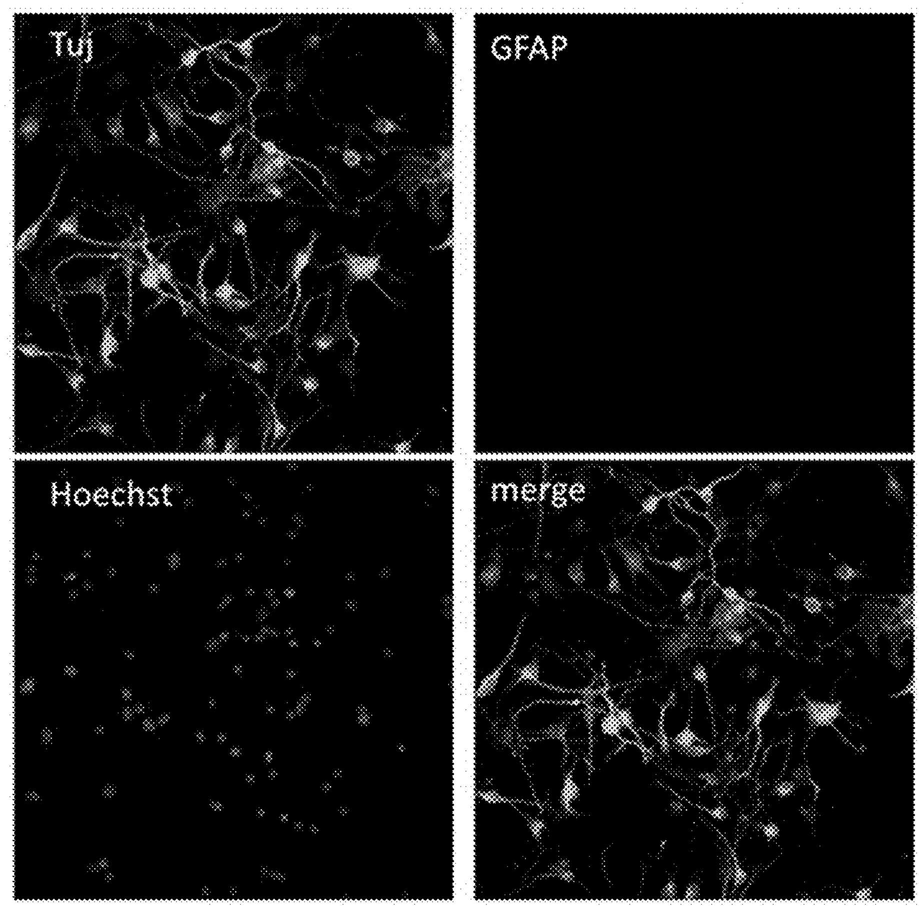
FIG. 4 shows that NVDCC-deficient mouse-derived neural stem cell neurospheres maintain the differentiation potential into a nerve cell even after repealing 80 passages (Example 1).

Further, increasing the number of passages of neural stem cells did not lead to (1) decrease in its self-propagation ability, and (2) loss of its differentiation potential into nerve cells. Rather, differentiation potential into nerve cells increased and glial production ability was reduced in response to differentiation induction stimulation. The results are shown in FIG. 4. In FIG. 4, Tuj-1-positive cells indicate nerve cells and GFAP-positive cells indicate glial cells. Moreover, Hoechst stains the cell nucleus.

Accordingly, NVDCC-deficient mouse-derived neural stem cells have increased passage ability comparable to unlimited passage ability, aid enables supplying of a large amount of primary culture nerve cells.

Example 2

Proliferation Ability of WT Mouse-Derived Neural Stem Cells that were Applied N-Type Calcium Channel (NVDCC)-Specific Inhibitor, and Analysis of Differentiation Potential into Nerve Cells 1. Preparation and Passaging of WT Mouse-Derived Neural Stem Cells Preparation of neural stem cells was performed by the following method.

First, the forebrain of newborn 8-day old nice (C57BL6N, Charles River Laboratories Japan, Inc.) was resected by conventional means. The resected cell tissues were then separated into cells with Neural Tissue Dissociation Kit (#130-092-628, from Miltenyi Biotec GmbH).

Cells obtained as above were suspended in D-MEM/Ham's F-12 (1:1) medium (Catalog #11039-021, from Invitrogen Corporation) comprising each of (1)×1 B-27 Supplement (Catalog #12587010, from (GIBCO Inc.), (2)×1 N2-Supplement (Catalog #17502-048, from invitrogen Corporation), and (3)×1 Penicillin-Streptomycin mixed solution (Catalog #P4333, from Sigma-Aldrich Corporation), and prepared to $7\times10^5$ cells/ml.

Subsequently, 10 ml of the cell suspension prepared as above was seeded in each of multiple 25 $cm^2$ flasks. FGF-b (Catalog #450-33, from peprotech) and EGF (Catalog #315-09, from Peprotech) each at a final concentration of 25 ng/ml were further added.

The cell suspensions seeded in the above flasks were divided into two groups.

In the "first group," w-conotoxin GVIA (Catalog #4161-v, from PEPTIDE) was added at a final concentration of 1 μM in the presence of 15 mM KCl, and half of the medium was exchanged every 3 to 4 days. On day 14, neurospheres were collected/suspended, prepared to $4\times10^4$ cells/ml, seeded on a 24 well plate at 500 μl, and this was employed as the passage. Note that when passaging, a medium of the pre-passaging cell culture medium and the new medium mixed at 1:1 was employed.

In the "second group," culture and passaging was performed under the same conditions as the first group, except that culturing was without adding KCl and ω-conotoxin GVIA.

Figure 5:
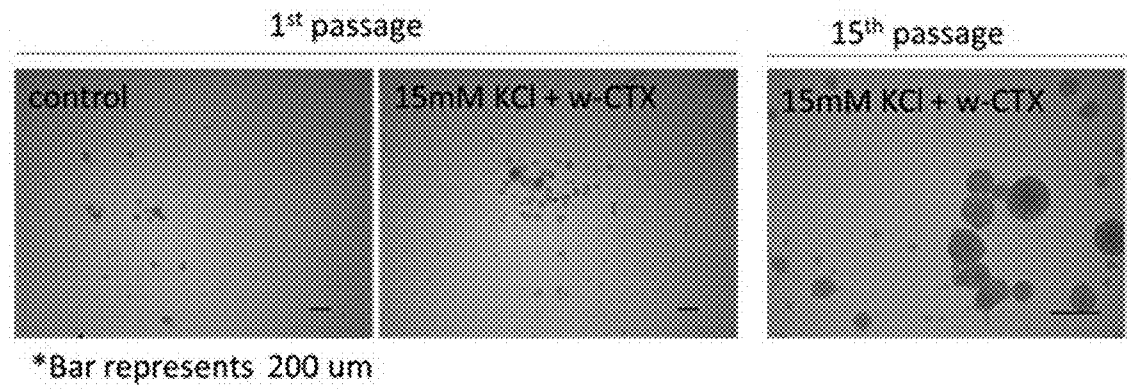
FIG. 5 shows the sphere-forming ability and the proliferation ability of WT mouse-derived neural stem cells that were applied an NVDCC-specific inhibitor (Example 2).
Figure 5:
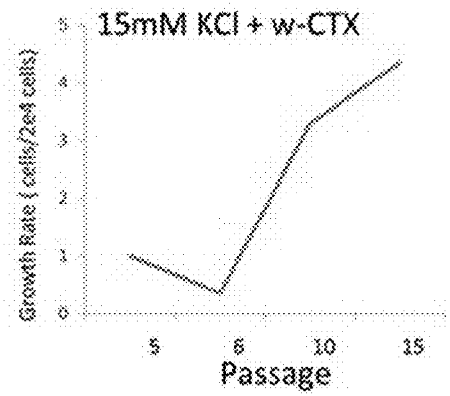

2. Observation of Sphere Formation and Proliferation Ability of WT Mouse-Derived Neural Stem Cells that were Applied NVDCC-Specific Inhibitor WT mouse-derived neural stem cells cultured without adding ω-conotoxin GVIA (i.e. the second group) after the 5th passage neither formed neurospheres nor proliferated and lead to cell death. On the other hand, WT mouse-derived neural stem cells with continued addition of ω-conotoxin GVIA the fast grow) could continue to form neurospheres while proliferating even after the 15th passage. The neurosphere images (photographs) and proliferation state in this experiment are shown in FIG. 5.

3. Differentiation Potential into Nerve Cells of WT Mouse-Derived Neural Stem Cells that were Applied NVDCC-Specific Inhibitor WT mouse-derived neural stem cell neurospheres diet the 15th passage performed by continued addition of ω-conotoxin GVIA in the presence of 15 mM KCl were seeded on a slide glass coated with poly-L-ornithine (Catalog #P3655, from sigma corporation) and laminin (Catalog #23017-015, from invitrogen Corporation), and differentiation was induced in a medium where both EGF and FGF-b are absent at 37° C. for 3 days.

The cultured cells were fixed with 4% PFA/PBS at 4° C. for 20 minutes, and washed twice with PBS at 4° C. for 10 minutes. Thai, said cells were permeabilized with 0.1% Triton X-100/PBS at room temperature for 15 minutes. Said permeabilized cells were then subjected to 20 minutes of blocking with Block Ace (from DS Pharma Biomedical Co., Ltd.) at room temperature. Subsequently, said blocked cells were reacted with a solution comprising a primary antibody (10% Block Ace, 0.1% Triton X-100/PBS) at room temperature for 1 hour, and then continued to react overnight at 4° C. On the next day, this was washed three times with 0.1% Triton X-100/PBS at room temperature for 10 minutes, and reacted with a solution comprising a fluorescently labeled secondary antibody (from Jackson: the product number of the secondary antibody for primary antibody Tuj-1 is 715-096-151, and the product number of the secondary antibody for primary antibody GFAP is 711-166-152) (10 μg/ml of secondary antibody, 10% Block Ace, 0.1% Triton X-100/PBS) at room temperature for 30 minutes. This was then washed with PBS at room temperature, mounted by conventional means and observed.

The following were used as primary antibodies.

Tuj-1: purchased from Covance (Catalog #: COVANCE #MMS-435P)

GFAP: purchased from DAKO (Catalog #: DAKO #Z0334)

Figure 6:
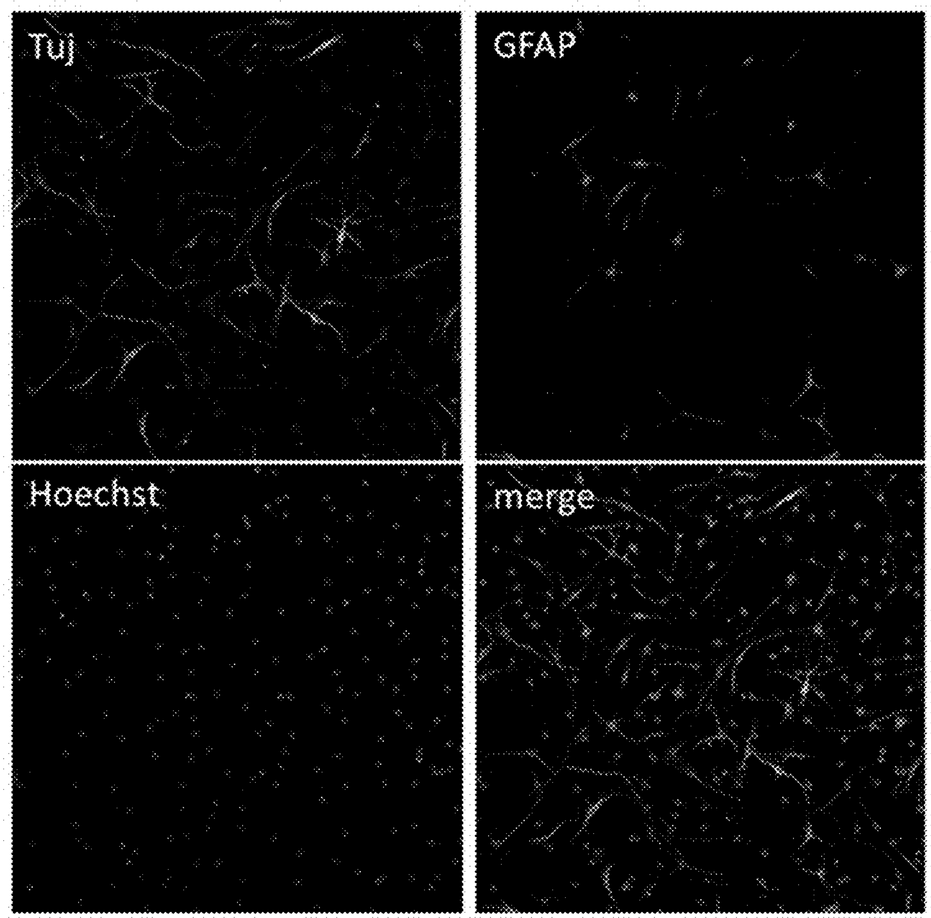
FIG. 6 shows that WT mouse-derived neural stem cells that were applied an NVDCC-specific inhibitor are differentiated into Tuj1-positive nerve cells and GFAP-positive astrocytes (Example 2).

As a result, differentiation into Tuj-1 (class III β-tubulin)-positive nerve cells and GFAP (grail fibrillary acidic protein)-positive astrocytes could be confirmed (FIG. 6).

Accordingly, it was shown that similarly to NVDCC-deficient mouse-derived neural stem cells, it is possible to passage wild type neural stem cells for along film by inhibiting the N-type calcium channel (NVDCC) with an inhibitor. It was also shown that neural stem cells passaged by this method, similarly to NVDCC-deficient mouse-derived neural stem cells, continue to retain differentiation potential into nerve cells.

In other words, passaging dose to unlimited culturing of neural stem cells can be performed either by inhibiting the N-type calcium channel (NVDCC) with an inhibitor (Example 2) or by genetically knocking out the N-type calcium channel gene (Example 1), and supplying of a large amount of primary culture nerve cells is enabled.

Example 3

Analysis of Proliferation Ability of Human-Derived Neural Progenitor Cells that were Applied NVDCC-Specific Inhibitor Genetically unmodified human neural progenitor cells (NHNP) (the number of passages 1: recorded at the time of purchase) were purchased from Lonza Walkersville Inc. (Walkersville, Md.).

Said cells frozen with liquid nitrogen were thawed at 37° C. by conventional means, and seeded on a low-cell-binding dish (90 mm in diameter, Nunc) supplemented with 14 mL of Bullet Kit™ medium. On the next day, neurospheres formed from NHNP were collected by centrifugation (120×g, 5 minutes).

The cells were subsequently divided into two groups. The "first group" as cultured in Bullet Kit™ medium comprising 100 nM of filter sterilized co-conotoxin GVIA (ω-CTX, Peptide Institute Inc., Osaka, Japan). The "second group" was cultured with Bullet Kit™ medium without ω-conotoxin GVIA. For each group, the medium was exchanged 3 times a week. Moreover, for each group, cells were passaged once every 7 to 10 days.

Neurospheres formed from the proliferated cells were collected by centrifugation (120×g, 5 minutes). The neurospheres were dispersed by treating with Accutase (Innovative Cell Technologies, Inc., San Diego, Calif.) at 37° C. for 10 minutes (i.e. suspended as single cells). This was centrifuged at 310×g for 5 minutes, and the pellets obtained were suspended in each medium.

Most NHNP formed large neurospheres at early culture stage (i.e. the stage before dividing the cells into two groups).

Figure 7:
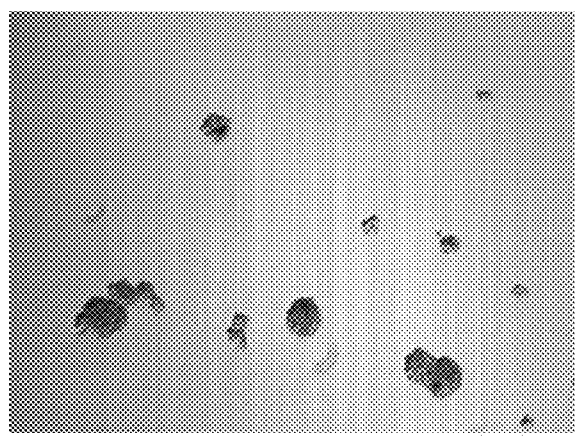
FIG. 7 shows that human-derived neural progenitor cells that were applied an NVDCC-specific inhibitor maintain the ability to repeatedly form neurospheres even after the 6th passage (Example 3).

However, at the stage after dividing the cells into two groups, in the "second group" (i.e. the group cultured in a medium without ω-CTX), cells obtained by dispersing the neurospheres could not form neurospheres in an ordinary medium, and survival was stopped after the 2nd passage. In contrast, in the "first group" (i.e. the group cultured in a medium comprising ω-CTX), cells obtained by dispersing the neurospheres maintained the ability to repeatedly form neurospheres even after the 6th passage (FIG. 7). From this result, it is seen that the passage ability of human neural progenitor cells is increased by inhibiting the N-type calcium channel (NVDCC) with ω-CTX.

Example 4

Glutamatergic Activity and Cholinergic Activity of Nerve Cells Differentiated from NVDCC-Deficient Mouse Lateral Ventricle-Derived Neural Stem Cells NVDCC-deficient mouse lateral vide-derived neural stem cells were maintained in culture in neurospheric form in Dulbecco's modified Eagle's medium Nutrient mixture F-12 Ham medium (Sigma-Aldrich) comprising (1) 1% N2 supplement (Invitrogen), (2) 2% B-27 supplement (Invitrogen), (3) 25 ng/ml of mouse basic FGF (PeproTech Inc.), and (4) 25 ng/ml of mouse epithelium proliferative factor (Invitrogen).

Half the medium amount was exchanged twice a week. Neurospheres were passaged over 30 to 40 generations, and then dispersed into single cells with NeuroCult (Stemcell Technologies).

Figure 8:
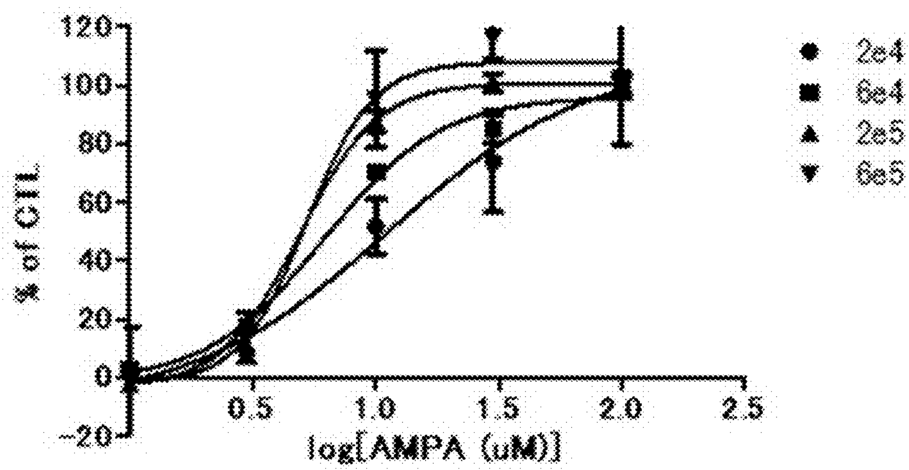
FIG. 8 shows that a nerve cell differentiated from an NVDCC-deficient mouse lateral ventricle-derived neural stem cell (differentiated neuron) differentiates into a nerve cell having a glutamic acid receptor which is activated by AMPA (Example 4).
Figure 9:
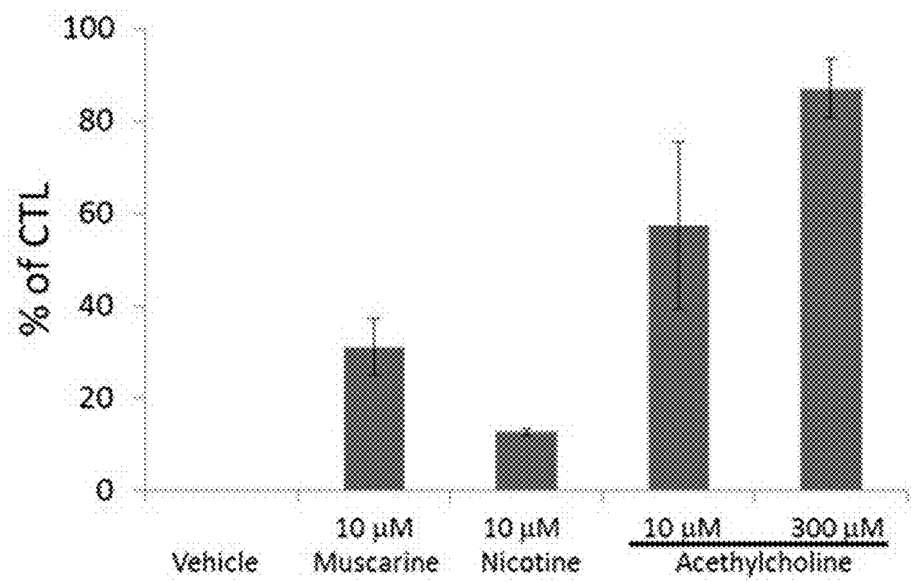
FIG. 9 shows that a nerve cell differentiated from an NVDCC-deficient mouse lateral ventricle-derived neural stem cell (differentiated neuron) differentiates into a nerve cell having an acetylcholine receptor comprising a muscarine receptor subtype and a nicotine receptor subtype (Example 4).

Cells dispersed into single cells obtained as such were seeded in a 96 BIOCOAT Poly-D-Lysine black/dean aware (Becton Dickinson) at cell densities of $2\times10^4$, $6\times10^4$, 2×10, and $6\times10^5$ cells/200 μL/well (corresponding to "2e4," "6e4," "2e5," and "6e5" in FIG. 8, respectively) or $6\times10^4$ cells/200 μL/well (FIG. 9).

The seeded cells were subsequently differentiated in a medium without a proliferative factor at 37° C. under 5% $CO_2$ condition for 2 weeks.

To the differentiated cells was added Calcium 5 dye (Molecular Devices) at 37° C. for 1 hour, and the ion channel activity was measured with Hamamatsu FDSS 6000 plate reader and liquid handling system.

The background fluorescence intensity (excitation wavelength 480 nm, emission wavelength 540 nm) was first monitored for 12 seconds, a ligand solution (AMPA (α-amino-3-hydroxy-5-methylisoxazole-4-propionic add), from Tocris Bioscience), acetylcholine (from Sigma-Aldrich Corporation), muscarine (from Sigma-Aldrich Corporation), and nicotine (from Sigma-Aldrich Corporation)) were then added at once at 20 μl/well, and the receptors shown in FIGS. 8 and 9 (glutamic acid receptor, muscarinic receptor, and acetylcholine receptor comprising nicotinic receptor) were activated Under this condition, the fluorescence reaction was captured at 0.3 second intervals for 93 seconds.

The data was analyzed, and normalized against the maximum reaction rate for each compound (CTL %). The sigmoid dose response curve was calculated with Prism software (MDF Co., Ltd.) (FIGS. 8 and 9). The dose of the compound used is as shown in the figures.

NVDCC-deficient mouse lateral ventricle neural stem cell-derived nerve cells (differentiated neurons) reacted to AMPA in a runner dependent on the dose and the number of cells (FIG. 8). The EC50 of each conditions of $2\times10^4$, $6\times10^4$, $2\times10^5$, and $6\times10^5$ cells/well were 11.3 μM, 6.5 μM, 5.0 μM, and 5.1 μM, respectively. Said cells also concentration-dependently reacted to acetylcholine. Said cells also reacted to muscarine and nicotine (FIG. 9).

In other words, it was shown that nerve cells obtained by differentiating the neural stem cells of the present invention have properties similar to ordinary nerve cells in regards to response to a neurotransmitter.

Example 5

Electrophysiological Analysis of Nerve Cells Produced from NVDCC-Deficient Mouse-Derived Neural Stem Cells NVDCC-deficient mouse hippocampus-derived neural stem cells were seeded on a multi-electrode dish (MED-P210A, Alpha MED Scientific Inc.) coated in advance with 0.1 ng/ml of poly-D-lysine (Sigma-Aldrich), and differentiated at 37° C. under 5% $CO_2$ condition for 6 weeks.

During the differentiation step, said cells were maintained in Dulbecco's modified Eagle's medium Nutrient mixture F-12 Ham medium (Sigma-Aldrich) (without proliferative factor) comprising (1) N2 supplement (Invitrogen) and (2) B-27 supplement (Invitrogen), and half the medium amount was exchanged twice a week.

During the electrophysiological test, the differentiated cells (differentiated neurons) on the MED probe were left standing in a small incubator (37° C.). Electric field potential that occurred at probes at 64 locations were all recorded with a multi-channel recording system (MED64 system; Alpha MED Science) at a sampling speed of 20 kHz, and at the same time filtered with a 100 Hz passband filter. The baseline threshold of electric potential by spontaneous activity of the neurons was measured for each experiment, and the change in average frequency was recorded after adding 1 mM of 4-aminopyridine (4-AP) (FIG. 10) or 100 nM of tetradotoxin (TTX) (FIG. 11).

Figure 10:
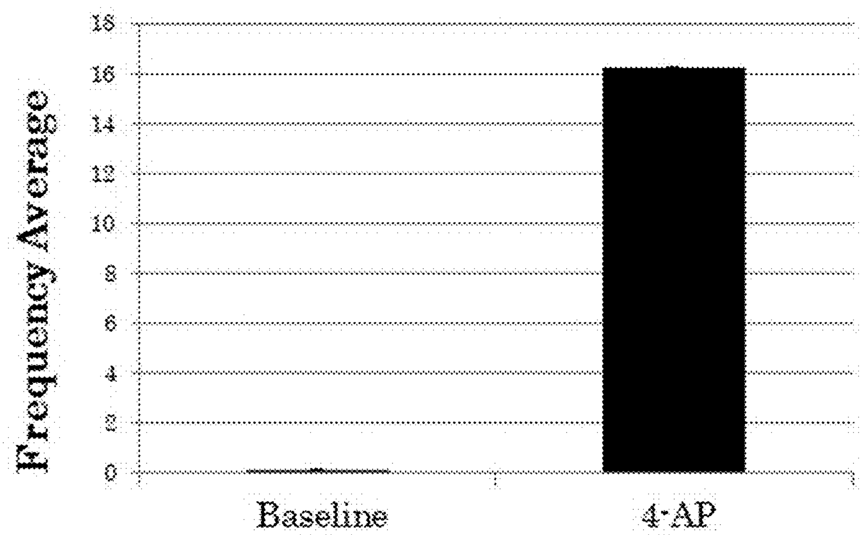
FIG. 10 shows that activity potential is significantly increased by 4-AP by differentiation induction of an NVDCC-deficient mouse-derived neural stem cell (Example 5).

The threshold was set at ±0.007 mV for the 4-AP activation experiment, and at −0.015 to 0.005 mV for the TTX suppression experiment. Spike frequency (Hz) exceeding the threshold was averaged. For the 4-AP activation experiment, the baseline activity and activity after stimulation were measured for 210 seconds and 490 seconds, respectively. For the TTX suppression experiment, both baseline activity and activity diet stimulation were measured for 180 seconds. The average values and standard error bats are shown in FIGS. 10 and 11.

Spontaneous activity potential was observed when NVDCC-deficient mouse hippocampus-derived neural stem cells were induced to differentiate for 6 weeks. The cell body of the differentiated neurons must be in contact with the electrode probe in order to record neuron activity potential. 56 probes (4-AP activation experiment) and 15 probes (TTX suppression experiment) out of 64 probes recorded reaction activity potential (FIG. 10). From this result, it was confirmed that neuronal cell bodies were in contact with the electrode probe and the measurement of action potential was carried out normally in this experiment.

Figure 11:
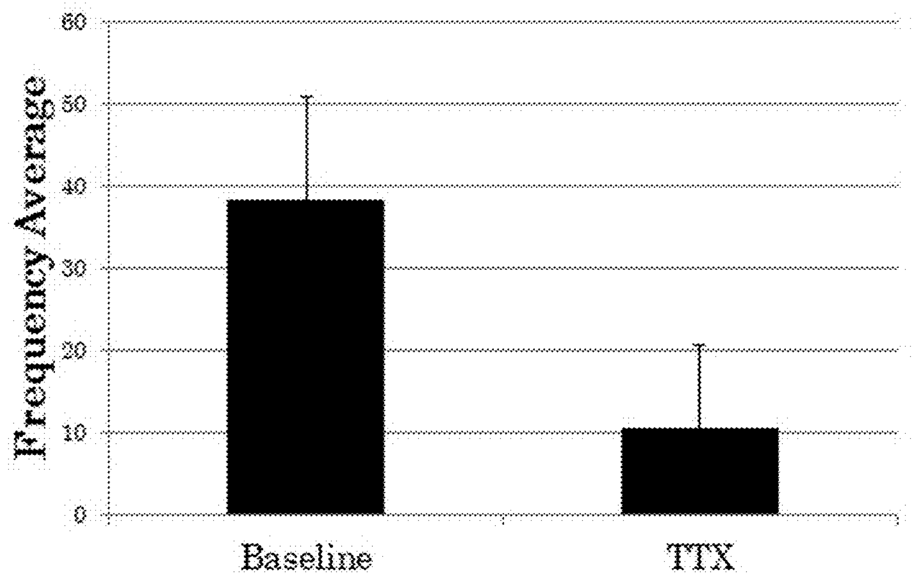
FIG. 11 shows that activity potential is suppressed by TTX by differentiation induction of an NVDCC-deficient mouse-derived neural stem cell (Example 5).

Further, the activity potential of the differentiated neurons was significantly increased by 4-AP (FIG. 10) and suppressed by TTX (FIG. 11). From this result, it was seen that evaluation of agents cube electrophysiologically performed by employing nerve cells differentiated from the neural stem cells of the present invention.

Example 6

Differentiation Potential Analysis of Human-Derived Neural Progenitor Cells that were Applied NVDCC-Specific Inhibitor 1. Preparation and Passaging of Human-Derived Neural Progenitor Cells that were Applied NVDCC-Specific Inhibitor Genetically unmodified human neural progenitor cells (NHNP) (the number of passages 1: recorded at the time of purchase) were purchased from Lonza Walkersville Inc. (Walkersville, Md.).

Said cells frozen with liquid nitrogen were thawed at 37° C. by conventional means, and seeded on a low-cell-binding dish (60 mm in diameter, Nunc) supplemented with 14 mL of NPMM Bullet Kit™ medium (Lonza, Catalog #CC3209). On the next day, neurospheres formed from NHNP were collected by centrifugation (90×g, 3 minutes).

The cells were subsequently divided into two groups. The "first grow" was cultured with NPMM Bullet Kit™ medium comprising 1 μM of filter sterilized ω-conotoxin GVIA (ω-CTX, Peptide Institute Inc., Osaka, Japan). The "second group" was cultured with Bullet Kit™ medium without co-conotoxin GVIA. For each group, the medium was exchanged 3 times a week. Moreover, for each group, cells were passaged once every 4 to 7 days.

Neurospheres famed from the proliferated cells were collected by centrifugation (90×g, 3 minutes). The neurospheres were dispersed by treating with Accutase (Innovative Cell Technologies, Inc., San Diego, Calif.) at room temperature for 5 minutes (i.e. suspended as single cells). This was centrifuged at 200×g for 5 minutes, and the pellets obtained were suspended in each medium.

Most NHNP formed large neurospheres at early culture stage (i.e. the stage before dividing the cells into two groups).

Figure 12:
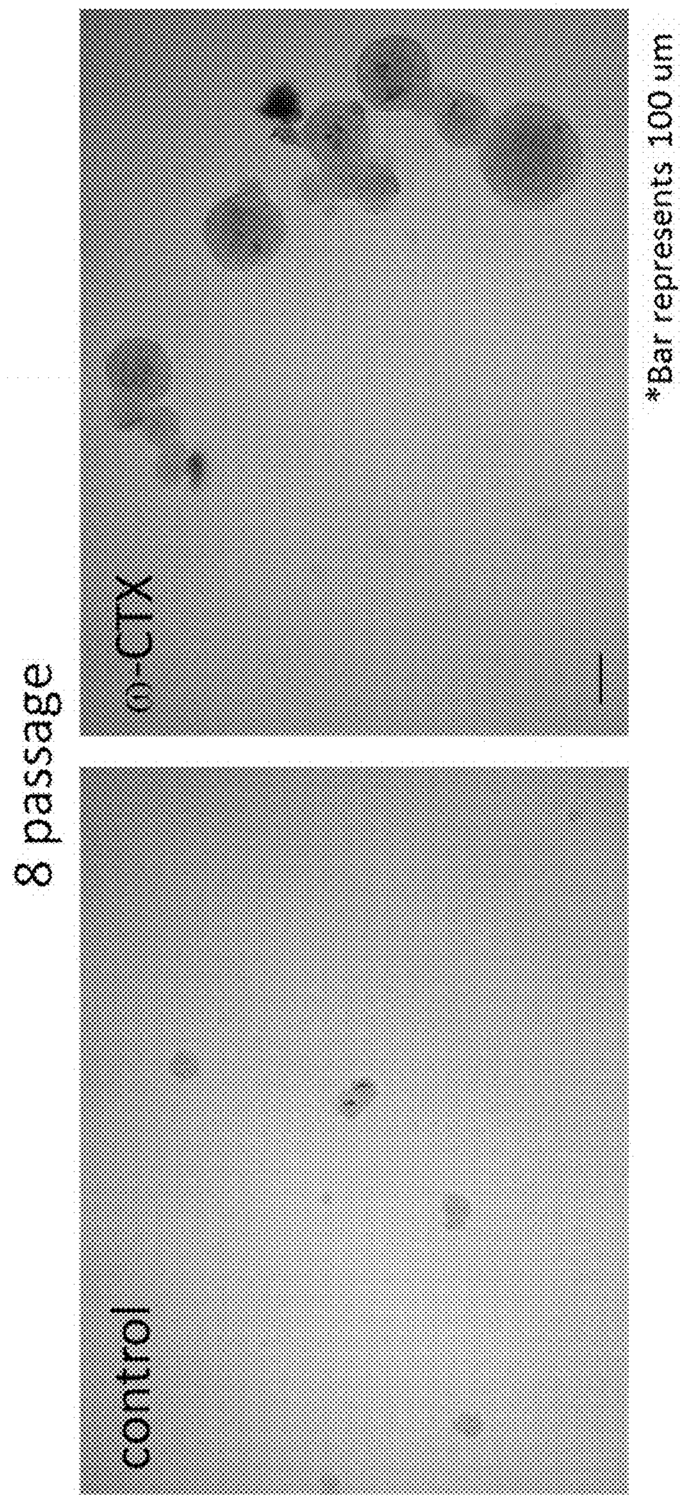
FIG. 12 shows that human-derived neural progenitor cells that were applied an NVDCC-specific inhibitor maintain the ability to repeatedly form neurospheres even after the 8th passage (Example 6).

However, at the stage after dividing the cells into two groups, in the "second group" (i.e. the group cultured in a medium without ω-CTX), cells obtained by dispersing the neurospheres could not form large neurospheres in an ordinary medium, and proliferation was gradually reduced. In contrast, in the "first group" (i.e. the group cultured in a medium comprising ω-CTX), cells obtained by dispersing the neurospheres maintained the ability to repeatedly form neurospheres even after the 20th passage. The appearance of neurosphere formation at the 8th passage for the fast group is shown in FIG. 12.

2. Differentiation Potential into Nerve Cells of Human-Derived Neural Progenitor Cells that were Applied NVDCC-Specific Inhibitor Human-derived neural progenitor cell neurospheres the 8th passage cultured in the presence of ω-conotoxin GVIA were seeded on a slide glass coated with poly-L-ornithine (Catalog #P3655, from sigma corporation) and laminin (Catalog #23017-015, from invitrogen Corporation), and differentiation induced in a medium where both EGF and FGF-b are absent at 37° C. for 3 days.

The cultured cells were fixed with 4% PFA/PBS at 4° C. for 20 minutes, and washed twice with PBS at 4° C. for 10 minutes. Then, said cells were permeabilized with 0.1% Triton X-100/PBS at room temperature for 15 minutes. Said permeabilized cells were then subjected to 20 minutes of blocking with Block Ace (from DS Pharma Biomedical Co., Ltd.) at room temperature. Subsequently, said blocked cells were reacted with a solution comprising a primary antibody (10% Block Ace, 0.1% Triton X-100/PBS) at room temperature for 1 hour, and then continued to react overnight at 4° C. On the next day, this was washed three times with 0.1% Triton X-100/PBS at room temperature for 10 minutes, and reacted with a solution comprising a fluorescently labeled secondary antibody (from Jackson: the product number of the secondary antibody for primary antibody Tuj-1 is 715-096-151, and the product number of the secondary antibody for primary antibody GFAP is 711-166-152) (10 μg/ml of secondary antibody, 10% Block Ace, 0.1% Triton X-100/PBS) at room temperature for 30 minutes. This was then washed with PBS at room temperature, mounted by conventional means and observed.

The following were used as primary antibodies.

Tuj-1: purchased from Covance (Catalog #: COVANCE #MMS-435P)

GFAP: purchased from DAKO (Catalog #: DAKO #Z0334)

Figure 13:
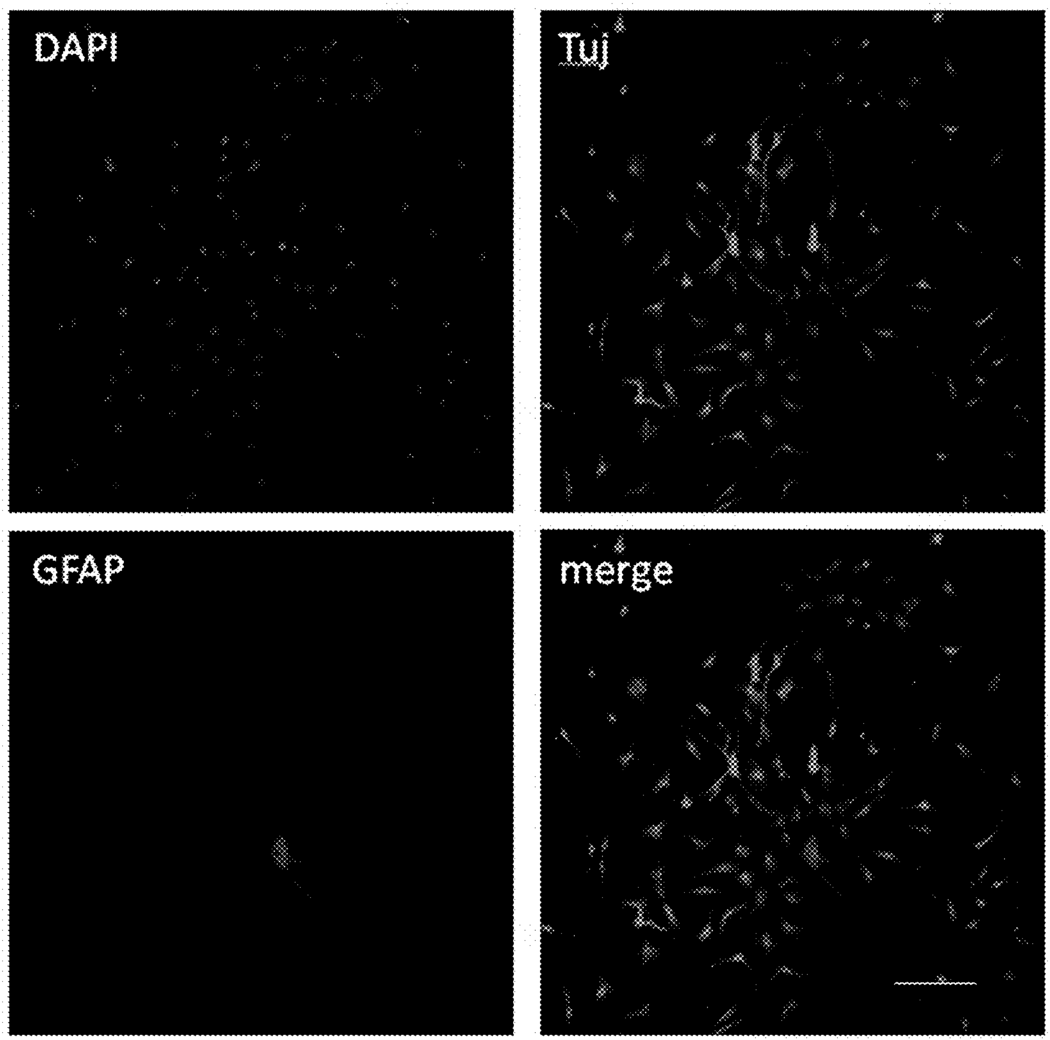
FIG. 13 shows that human-derived neural progenitor cells that were applied an NVDCC-specific inhibitor are differentiated into Tuj1-positive nerve cells and GFAP-positive astrocytes (Example 6).

As a result, it could be confirmed that many cells differentiate into Tuj-1 (class III β-tubulin)-positive nerve cells and some cells differentiate into GFAP (grail fibrillary acidic protein)-positive astrocytes (FIG. 13).

Accordingly, it was shown that similarly to mouse-derived neural stem cells, it is possible to passage human neural progenitor cells for along time while retaining the differentiation potential into a nerve cell by inhibiting the N-type calcium channel (NVDCC) with an inhibitor.

The invention claimed is:

1. A neural stem cell having the following characteristics:

(a) function or expression of the N-type calcium channel is knocked out in the cell, (b) influx of Ca2+ via the N-type calcium channel is substantially absent when function or expression of the N-type calcium channel is knocked out in the cell, (c) the cell can be passaged for at least 4 generations, and (d) the cell maintains differentiation potential into a nerve cell after passage for 4 generations.

2. The neural stem cell according to claim 1, wherein the gene encoding the α1B subunit of the N-type calcium channel is knocked out.

3. The neural stem cell according to claim 1, wherein the neural stem cell is nestin-positive after passage for 4 generations.

4. The neural stem cell according to claim 1, wherein the neural stem cell has high proliferation ability and high sphere-forming ability after passage for 4 generations.

5. The neural stem cell according to claim 1, wherein function or expression of the N-type calcium channel is knocked out by contacting the neural stem cell with an agent that inhibits function or expression of the N-type calcium channel.

6. The neural stem cell according to claim 5, wherein the agent is ω-conotoxin GVIA.

7. A method for manufacturing a neural stem cell, wherein the method comprises:

(A) a step of preparing a neural stem cell in vitro, and (B) a step of knocking out function or expression of the N-type calcium channel of the neural stem cell in vitro, wherein the manufactured neural stem cell has the following characteristics:

(a) function or expression of the N-type calcium channel is knocked out in the cell, (b) influx of Ca2+ via the N-type calcium channel is substantially absent when function or expression of the N-type calcium channel is knocked out in the cell, (c) the cell can be passaged for at least 4 generations, and (d) the cell maintains differentiation potential into a nerve cell after passage for 4 generations.

8. The method for manufacturing a neural stem cell according to claim 7, wherein the neural stem cell in step (A) is a cell derived from a human.

9. The method for manufacturing a neural stem cell according to claim 7, wherein the neural stem cell in step (A) is a neural stem cell prepared by differentiation induction of an embryonic stem (ES) or induced pluripotent stem (iPS) cell into a neural stem cell.

10. The method for manufacturing a neural stem cell according to claim 7, wherein the gene encoding the $\alpha$1B subunit of the N-type calcium channel is knocked out.

11. The method for manufacturing a neural stem cell according to claim 7, wherein function or expression of the N-type calcium channel is knocked out by contacting the neural stem cell with an agent that inhibits function or expression of the N-type calcium channel.

12. The method for manufacturing a neural stem cell according to claim 11, wherein the agent is $\omega$-conotoxin GVIA.

* * * * *

SEQUENCE LISTING

<160> NUMBER OF SEQ ID NOS: 7

<210> SEQ ID NO 1
<211> LENGTH: 9805
<212> TYPE: DNA
<213> ORGANISM: Homo sapiens

<400> SEQUENCE: 1

```
gcggcggcgg ctgcggcggt ggggccgggc gaggtccgct gcggtcccgg cggctccgtg      60
gctgctccgc tctgagcgcc tggcgcgccc cgcgccctcc ctgccggggc cgctgggccg     120
gggatgcacg cggggcccgg gagccatggt ccgcttcggg gacgagctgg gcggccgcta     180
tgggggcccc ggcggcggag agcgggcccg gggcggcggg gccggcgggg cgggggggcc     240
gggtcccggg gggctgcagc ccggccagcg ggtcctctac aagcaatcga tcgcgcagcg     300
cgcgcggacc atggcgctgt acaaccccat cccggtcaag cagaactgct tcaccgtcaa     360
ccgctcgctc ttcgtcttca gcgaggacaa cgtcgtccgc aaatacgcga agcgcatcac     420
cgagtggcct ccattcgagt atatgatcct ggccaccatc atcgccaact gcatcgtgct     480
ggccctggag cagcacctcc ctgatgggga caaaacgccc atgtccgagc ggctggacga     540
cacggagccc tatttcatcg ggatcttttg cttcgaggca gggatcaaaa tcatcgctct     600
gggctttgtc ttccacaagg gctcttacct gcggaacggc tggaacgtca tggacttcgt     660
ggtcgtcctc acagggatcc ttgccacggc tggaactgac ttcgacctgc gaacactgag     720
ggctgtgcgt gtgctgaggc ccctgaagct ggtgtctggg attccaagtt tgcaggtggt     780
gctcaagtcc atcatgaagg ccatggttcc actcctgcag attgggctgc ttctcttctt     840
tgccatcctc atgtttgcca tcattggcct ggagttctac atgggcaagt tccacaaggc     900
ctgtttcccc aacagcacag atgcggagcc cgtgggtgac ttcccctgtg gcaaggaggc     960
```

-continued cccagcccgg ctgtgcgagg gcgacactga gtgccgggag tactggccag gacccaactt 1020
tggcatcacc aactttgaca atatcctgtt tgccatcttg acggtgttcc agtgcatcac 1080
catggagggc tggactgaca tcctctataa tacaaacgat gcggccggca acacctggaa 1140
ctggctctac ttcatccctc tcatcatcat cggctccttc ttcatgctca acctggtgct 1200
gggcgtgctc tcgggggagt ttgccaagga gcgagagagg gtggagaacc gccgcgcctt 1260
cctgaagctg cgccggcagc agcagatcga gcgagagctc aacgggtacc tggagtggat 1320
cttcaaggcg gaggaagtca tgctggccga ggaggacagg aatgcagagg agaagtcccc 1380
tttggacgtg ctgaagagag cggccaccaa gaagagcaga aatgacctga tccacgcaga 1440
ggagggagag gaccggtttg cagatctctg tgctgttgga tccccccttcg cccgcgccag 1500 cctcaagagc gggaagacag agagctcgtc atacttccgg aggaaggaga agatgttccg 1560 gtttttatc cggcgcatgg tgaaggctca gagcttctac tgggtggtgc tgtgcgtggt 1620
ggccctgaac acactgtgtg tggccatggt gcattacaac cagccgcggc ggcttaccac 1680
gaccctgtat tttgcagagt ttgttttcct gggtctcttc ctcacagaga tgtccctgaa 1740
gatgtatggc ctggggccca gaagctactt ccggtcctcc ttcaactgct tcgactttgg 1800
ggtcatcgtg ggagcgtct ttgaagtggt ctgggcggcc atcaagccgg gaagctcctt 1860
tgggatcagt gtgctgcggg ccctccgcct gctgaggatc ttcaaagtca cgaagtactg 1920
gagctccctg cggaacctgg tggtgtccct gctgaactcc atgaagtcca tcatcagcct 1980
gctcttcttg ctcttcctgt tcattgtggt cttcgccctg ctggggatgc agctgtttgg 2040
gggacagttc aacttccagg atgagactcc cacaaccaac ttcgacacct tccctgccgc 2100
catcctcact gtcttccaga tcctgacggg agaggactgg aatgcagtga tgtatcacgg 2160
gatcgaatcg caaggcggcg tcagcaaagg catgttctcg tccttttact tcattgtcct 2220
gacactgttc ggaaactaca ctctgctgaa tgtctttctg gccatcgctg tggacaacct 2280
ggccaacgcc caagagctga ccaaggatga agaggagatg gaagaagcag ccaatcagaa 2340
gcttgctctg caaaaggcca aagaagtggc tgaagtcagc cccatgtctg ccgcgaacat 2400
ctccatcgcc gccaggcagc agaactcggc caaggcgcgc tcggtgtggg agcagcgggc 2460
cagccagcta cggctgcaga acctgcgggc cagctgcgag gcgctgtaca gcgagatgga 2520
ccccgaggag cggctgcgct tcgccactac gcgccacctg cggcccgaca tgaagacgca 2580
cctggaccgg ccgctggtgg tggagctggg ccgcgacggc gcgcgggggc ccgtgggagg 2640
caaagcccga cctgaggctg cggaggcccc cgagggcgtc gaccctccgc gcaggcacca 2700
ccggcaccgc gacaaggaca agacccccgc ggcgggggac caggaccgag cagaggcccc 2760
gaaggcggag agcggggagc ccggtgcccg ggaggagcgg ccgcggccgc accgcagcca 2820
cagcaaggag gccgcggggc ccccggaggc gcggagcgag cgcggccgag gcccaggccc 2880
cgagggcggc cggcggcacc accggcgcgg ctccccggag gaggcggccg agcgggagcc 2940
ccgacgccac cgcgcgcacc ggcaccagga tccgagcaag gagtgcgccg gcgccaaggg 3000
cgagcggcgc gcgcggcacc gcggcggccc ccgagcgggg ccccgggagg cggagagcgg 3060
ggaggagccg gcgcggcggc accgggcccg gcacaaggcg cagcctgctc acgaggctgt 3120
ggagaaggag accacggaga aggaggccac ggagaaggag gctgagatag tggaagccga 3180
caaggaaaag gagctccgga accaccagcc ccgggagcca cactgtgacc tggagaccag 3240
tgggactgtg actgtgggtc ccatgcacac actgcccagc acctgtctcc agaaggtgga 3300

-continued

```
ggaacagcca gaggatgcag acaatcagcg gaacgtcact cgcatgggca gtcagccccc   3360
agacccgaac actattgtac atatcccagt gatgctgacg ggccctcttg gggaagccac   3420
ggtcgttccc agtggtaacg tggacctgga aagccaagca gaggggaaga aggaggtgga   3480
agcggatgac gtgatgagga gcggcccccg gcctatcgtc ccatacagct ccatgttctg   3540
tttaagcccc accaacctgc tccgccgctt ctgccactac atcgtgacca tgaggtactt   3600
cgaggtggtc attctcgtgg tcatcgcctt gagcagcatc gccctggctg ctgaggaccc   3660
agtgcgcaca gactcgccca ggaacaacgc tctgaaatac ctggattaca ttttcactgg   3720
tgtctttacc tttgagatgg tgataaagat gatcgacttg ggactgctgc ttcaccctgg   3780
agcctatttc cgggacttgt ggaacattct ggacttcatt gtggtcagtg gcgccctggt   3840
ggcgtttgct ttctcaggat ccaaagggaa agacatcaat accatcaagt ctctgagagt   3900
ccttcgtgtc ctgcggcccc tcaagaccat caaacggctg cccaagctca aggctgtgtt   3960
tgactgtgtg gtgaactccc tgaagaatgt cctcaacatc ttgattgtct acatgctctt   4020
catgttcata tttgccgtca ttgcggtgca gctcttcaaa gggaagtttt tctactgcac   4080
agatgaatcc aaggagctgg agagggactg caggggtcag tatttggatt atgagaagga   4140
ggaagtggaa gctcagccca ggcagtggaa gaaatacgac tttcactacg acaatgtgct   4200
ctgggctctg ctgacgctgt tcacagtgtc cacgggagaa ggctggccca tggtgctgaa   4260
acactccgtg gatgccacct atgaggagca gggtccaagc cctgggtacc gcatggagct   4320
gtccatcttc tacgtggtct actttgtggt ctttcccttc ttcttcgtca acatctttgt   4380
ggctttgatc atcatcacct tccaggagca gggggacaag gtgatgtctg aatgcagcct   4440
ggagaagaac gagagggctt gcattgactt cgccatcagc gccaaacccc tgacacggta   4500
catgccccaa aaccggcagt cgttccagta taagacgtgg acatttgtgg tctccccgcc   4560
ctttgaatac ttcatcatgg ccatgatagc cctcaacact gtggtgctga tgatgaagtt   4620
ctatgatgca ccctatgagt acgagctgat gctgaaatgc ctgaacatcg tgttcacatc   4680
catgttctcc atggaatgcg tgctgaagat catcgccttt ggggtgctga actatttcag   4740
agatgcctgg aatgtctttg actttgtcac tgtgttggga agtattactg atattttagt   4800
aacagagatt gcggaaacga acaatttcat caacctcagc ttcctccgcc tctttcgagc   4860
tgcgcggctg atcaagctgc tccgccaggg ctacaccatc cgcatcctgc tgtggacctt   4920
tgtccagtcc ttcaaggccc tgccctacgt gtgtctgctc attgccatgc tgttcttcat   4980
ctacgccatc atcggcatgc aggtgtttgg gaatattgcc ctggatgatg acaccagcat   5040
caaccgccac aacaacttcc ggacgttttt gcaagccctg atgctgctgt tcaggagcgc   5100
cacgggggag gcctggcacg agatcatgct gtcctgcctg agcaaccagg cctgtgatga   5160
gcaggccaat gccaccgagt gtggaagtga ctttgcctac ttctacttcg tctccttcat   5220
cttcctgtgc tcctttctga tgttgaacct ctttgtggct gtgatcatgg acaattttga   5280
gtacctcacg cgggactctt ccatcctagg tcctcaccac ttggatgagt tcatccgggt   5340
ctgggctgaa tacgacccgg ctgcgtgtgg gcgcatcagt tacaatgaca tgtttgagat   5400
gctgaaacac atgtccccgc ctctggggct ggggaagaaa tgccctgctc gagttgctta   5460
caagcgcctg gttcgcatga acatgcccat ctccaacgag gacatgactg ttcacttcac   5520
gtccacgctg atggccctca tccggacggc actggagatc aagctggccc cagctgggac   5580
aaagcagcat cagtgtgacg cggagttgag gaaggagatt tccgttgtgt gggccaatct   5640
gccccagaag actttggact tgctggtacc accccataag cctgatgaga tgacagtggg   5700
```

-continued

```
gaaggtttat gcagctctga tgatattcga cttctacaag cagaacaaaa ccaccagaga   5760
ccagatgcag caggctcctg gaggcctctc ccagatgggt cctgtgtccc tgttccaccc   5820
tctgaaggcc accctggagc agacacagcc ggctgtgctc cgaggagccc gggttttcct   5880
tcgacagaag agttccacct ccctcagcaa tggcggggcc atacaaaacc aagagagtgg   5940
catcaaagag tctgtctcct ggggcactca aaggacccag gatgcacccc atgaggccag   6000
gccacccctg gagcgtggcc actccacaga gatccctgtg gggcggtcag gagcactggc   6060
tgtggacgtt cagatgcaga gcataacccg gaggggccct gatggggagc cccagcctgg   6120
gctggagagc cagggtcgag cggcctccat gccccgcctt gcggccgaga ctcagcccgt   6180
cacagatgcc agccccatga agcgctccat ctccacgctg gcccagcggc cccgtgggac   6240
tcatctttgc agcaccaccc cggaccgccc acccccctagc caggcgtcgt cgcaccacca   6300
ccaccaccgc tgccaccgcc gcagggacag gaagcagagg tccctggaga aggggcccag   6360
cctgtctgcc gatatggatg gcgcaccaag cagtgctgtg gggccggggc tgcccccggg   6420
agaggggcct acaggctgcc ggcgggaacg agagcgccgg caggagcggg gccggtccca   6480
ggagcggagg cagccctcat cctcctcctc ggagaagcag cgcttctact cctgcgaccg   6540
ctttgggggc cgtgagcccc cgaagcccaa gccctccctc agcagccacc caacgtcgcc   6600
aacagctggc caggagccgg gaccccaccc acagggcagt ggttccgtga atgggagccc   6660
cttgctgtca acatctggtg ctagcacccc cggccgcggt gggcggaggc agctccccca   6720
gacgcccctg actccccgcc ccagcatcac ctacaagacg gccaactcct cacccatcca   6780
cttcgccggg gctcagacca gcctccctgc cttctcccca ggccggctca gccgtgggct   6840
ttccgaacac aacgccctgc tgcagagaga ccccctcagc cagcccctgg cccctggctc   6900
tcgaattggc tctgaccctt acctggggca gcgtctggac agtgaggcct ctgtccacgc   6960
cctgcctgag gacactctca ctttcgagga ggctgtggcc accaactcgg gccgctcctc   7020
caggacttcc tacgtgtcct ccctgacctc ccagtctcac cctctccgcc gcgtgcccaa   7080
cggttaccac tgcaccctgg gactcagctc gggtggccga gcacggcaca gctaccacca   7140
ccctgaccaa gaccactggt gctagctgca ccgtgaccgc tcagacgcct gcatgcagca   7200
ggcgtgtgtt ccagtggatg agttttatca tccacacggg gcagccggcc ctcgggggag   7260
gccttgccca ccttggtgag gctcctgtgg cccctccctc cccctcctcc cctcttttac   7320
tctagacgac gaataaagcc ctgttagagg atgcggctct ctctgtcccc ttcctgtcct   7380
gccttcctgg gtctcgtacc acacaccaga ccctaaaccg caggctgctg tgtgtggctg   7440
agaaggaccc aggagtccaa atcccgtgtc ctgggactca gcatccagca tgggtgcttg   7500
gagccgttgt gaggagctct gcgtcctgtg gggagcaccc ttcacgtggc cgtgcggcac   7560
agagaagcag ggcccacctg aaagtgcgcc gagacctcgg gacggagggg atggggaggg   7620
ggacacagtc gtggcttgtg cagcccgcca gtgtcagcga atgctcactc aggcaagctc   7680
tgtcctccct ggacaccgtc agccccacag gaaccgagct gggaagtgtt cttgctgtgg   7740
ttgtgatttt taattgcaac acctctcatt cttgtcactt ctatatacgt gatgtagaaa   7800
aaatggaaaa ccagaaaaat ggggaaggaa atgttcacat aactttaaaa aatcaaacct   7860
gtgaaagaaa gatgtcagct ttttgccacg tgtctttgtg gcttatgcga ggagactccc   7920
tgtgcagccc tgtccggtcc aggtggacgt agacggcccc tggctctgct gctcttgacc   7980
aagtgcctga ccgccaggcc ctcacaccca ggctcctggg cactgtggtg tgaggcgagg   8040
```

```
cctcgggatc catcaccgca ggatgctgtg aaaagtactc gcgatggcag ccaggtagca   8100
agcccttgcc agtggagagc actggatgtc atggtggcaa acaaggcagc catttgctgt   8160
cctcctccca cgagtggaag gggtttccaa ggaagccaca gggcagctga ccacgtgctt   8220
gtgtgaggca ttttcagtct gttctgcata tgattctcag ggcacactct gtggtatgtg   8280
aaataggttt ccttccacat acagcagaag agaggcaaag gctggtagga aggaggaaga   8340
cattggctgg gggcttggat gtggggccgt cagggcagga gggaggaagc cccagctgga   8400
atgaaactca gagcaagtga ccgagggagg acacggctcc tgccactgag gccgggcacc   8460
tgatgcccag cactgtcctg gcgccagaca cagggagcag gcagtcaagt gaggtctgac   8520
ccccatggcc acgctcagga gagaaagacc atgctcagga cactgtccaa ggtgcacaag   8580
atgctgggag gtcccttgtt tggtgaagaa agggagcatt tagagcagtt gatggtggtg   8640
tgtcctccgt gttctgaaat tccagatgat ctgtgttgga ttcttggctt ctaccccatg   8700
attctcctca aagaaattgt gtgtgatgtg tgtgtgtgtg tgtgtgtgtg tgtgtctgtg   8760
tcacaggaga tgcagtgcct gtacaggtgt gttcagtgtg tggatgtcat taacccatag   8820
ggctatgcaa caaaagacac atttaataga agtaaaacac acaagaccgc tgcctggtct   8880
cggggttcag catgattgtg accaaacctt tttatagaat ttccttacct gaaggcacaa   8940
cactctgaaa ctttaaagat aacagagtat tttattccaa tagaataaac caggaatctc   9000
ggactgtgca tgtgatcact gtgctcctgt tgcaaagtag aaggatgtgt attttgacac   9060
tgacgttttg tctcttgttc cccagccccc agcccatgtt atcttgggtg tcgaatgtgt   9120
ccattccatg cagaaccaca gccatttccc caggcagtgt tgggtcgaga atccactttt   9180
ctaaacccac acagcctagc tggcttgtct agactcttct aggcattgga attgatgaaa   9240
actacaggga gcggggaaag gagacattat gtcttgtttt cctgactttg ggttttgttt   9300
ctcactgtgt cttctccggc tatcatatat gtcccctgaa tctcatagtg agctgccaaa   9360
tttgaagtgc atcacccagt tgtctgcatc tggaaccagt caagcagtgg ctgtagtttg   9420
aacaagttat gtgtgcatgt aacatatata catatataca tatatacaag tatgtgcatg   9480
ataatgtata tcttcgtact ttttgataca atgtattcat ttgttaattt ttaattatat   9540
ttgatataaa tcaaaggttt gttgcaaaac tttatattta agaagtgtta aaaaaaaaaa   9600
aaagtcccaa ccatgcaaca caactgggac ctacttaaaa agaaattctg tgattgacta   9660
gtttgctgcc tgagtcatat ttatcagcca aactttggat tctgctgttg tttctacaat   9720
gacattttgt atgaagcaaa gtccttgaat taaaataaaa acttagcaaa aaatcaaaaa   9780
caaaacccca aaaaaaaaaa aaaaa                                         9805
```

<210> SEQ ID NO 2
<211> LENGTH: 2339
<212> TYPE: PRT
<213> ORGANISM: Homo sapiens

<400> SEQUENCE: 2

```
Met Val Arg Phe Gly Asp Glu Leu Gly Gly Arg Tyr Gly Gly Pro Gly
1               5                   10                  15

Gly Gly Glu Arg Ala Arg Gly Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60
```

```
Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Ala Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480
```

```
Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
                805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
        835                 840                 845

Arg Arg His His Arg His Arg Asp Lys Asp Lys Thr Pro Ala Ala Gly
    850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                885                 890                 895

Ala Gly Pro Pro Glu Ala Arg Ser Glu Arg Gly Arg Gly Pro Gly Pro
```

```
            900                 905                 910

Glu Gly Gly Arg Arg His His Arg Arg Gly Ser Pro Glu Glu Ala Ala
        915                 920                 925

Glu Arg Glu Pro Arg Arg His Arg Ala His Arg His Gln Asp Pro Ser
    930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
            980                 985                 990

Glu Lys Glu Thr Thr Glu Lys Glu  Ala Thr Glu Lys Glu  Ala Glu Ile
        995                 1000                1005

Val Glu  Ala Asp Lys Glu Lys  Glu Leu Arg Asn His  Gln Pro Arg
    1010                1015                1020

Glu Pro  His Cys Asp Leu Glu  Thr Ser Gly Thr Val  Thr Val Gly
    1025                1030                1035

Pro Met  His Thr Leu Pro Ser  Thr Cys Leu Gln Lys  Val Glu Glu
    1040                1045                1050

Gln Pro  Glu Asp Ala Asp Asn  Gln Arg Asn Val Thr  Arg Met Gly
    1055                1060                1065

Ser Gln  Pro Pro Asp Pro Asn  Thr Ile Val His Ile  Pro Val Met
    1070                1075                1080

Leu Thr  Gly Pro Leu Gly Glu  Ala Thr Val Val Pro  Ser Gly Asn
    1085                1090                1095

Val Asp  Leu Glu Ser Gln Ala  Glu Gly Lys Lys Glu  Val Glu Ala
    1100                1105                1110

Asp Asp  Val Met Arg Ser Gly  Pro Arg Pro Ile Val  Pro Tyr Ser
    1115                1120                1125

Ser Met  Phe Cys Leu Ser Pro  Thr Asn Leu Leu Arg  Arg Phe Cys
    1130                1135                1140

His Tyr  Ile Val Thr Met Arg  Tyr Phe Glu Val Val  Ile Leu Val
    1145                1150                1155

Val Ile  Ala Leu Ser Ser Ile  Ala Leu Ala Ala Glu  Asp Pro Val
    1160                1165                1170

Arg Thr  Asp Ser Pro Arg Asn  Asn Ala Leu Lys Tyr  Leu Asp Tyr
    1175                1180                1185

Ile Phe  Thr Gly Val Phe Thr  Phe Glu Met Val Ile  Lys Met Ile
    1190                1195                1200

Asp Leu  Gly Leu Leu Leu His  Pro Gly Ala Tyr Phe  Arg Asp Leu
    1205                1210                1215

Trp Asn  Ile Leu Asp Phe Ile  Val Val Ser Gly Ala  Leu Val Ala
    1220                1225                1230

Phe Ala  Phe Ser Gly Ser Lys  Gly Lys Asp Ile Asn  Thr Ile Lys
    1235                1240                1245

Ser Leu  Arg Val Leu Arg Val  Leu Arg Pro Leu Lys  Thr Ile Lys
    1250                1255                1260

Arg Leu  Pro Lys Leu Lys Ala  Val Phe Asp Cys Val  Val Asn Ser
    1265                1270                1275

Leu Lys  Asn Val Leu Asn Ile  Leu Ile Val Tyr Met  Leu Phe Met
    1280                1285                1290

Phe Ile  Phe Ala Val Ile Ala  Val Gln Leu Phe Lys  Gly Lys Phe
    1295                1300                1305
```

```
Phe Tyr  Cys Thr Asp Glu Ser  Lys Glu Leu Glu Arg  Asp Cys Arg
    1310                 1315                 1320

Gly Gln  Tyr Leu Asp Tyr Glu  Lys Glu Glu Val Glu  Ala Gln Pro
    1325                 1330                 1335

Arg Gln  Trp Lys Lys Tyr Asp  Phe His Tyr Asp Asn  Val Leu Trp
    1340                 1345                 1350

Ala Leu  Leu Thr Leu Phe Thr  Val Ser Thr Gly Glu  Gly Trp Pro
    1355                 1360                 1365

Met Val  Leu Lys His Ser Val  Asp Ala Thr Tyr Glu  Glu Gln Gly
    1370                 1375                 1380

Pro Ser  Pro Gly Tyr Arg Met  Glu Leu Ser Ile Phe  Tyr Val Val
    1385                 1390                 1395

Tyr Phe  Val Val Phe Pro Phe  Phe Phe Val Asn Ile  Phe Val Ala
    1400                 1405                 1410

Leu Ile  Ile Ile Thr Phe Gln  Glu Gln Gly Asp Lys  Val Met Ser
    1415                 1420                 1425

Glu Cys  Ser Leu Glu Lys Asn  Glu Arg Ala Cys Ile  Asp Phe Ala
    1430                 1435                 1440

Ile Ser  Ala Lys Pro Leu Thr  Arg Tyr Met Pro Gln  Asn Arg Gln
    1445                 1450                 1455

Ser Phe  Gln Tyr Lys Thr Trp  Thr Phe Val Val Ser  Pro Pro Phe
    1460                 1465                 1470

Glu Tyr  Phe Ile Met Ala Met  Ile Ala Leu Asn Thr  Val Val Leu
    1475                 1480                 1485

Met Met  Lys Phe Tyr Asp Ala  Pro Tyr Glu Tyr Glu  Leu Met Leu
    1490                 1495                 1500

Lys Cys  Leu Asn Ile Val Phe  Thr Ser Met Phe Ser  Met Glu Cys
    1505                 1510                 1515

Val Leu  Lys Ile Ile Ala Phe  Gly Val Leu Asn Tyr  Phe Arg Asp
    1520                 1525                 1530

Ala Trp  Asn Val Phe Asp Phe  Val Thr Val Leu Gly  Ser Ile Thr
    1535                 1540                 1545

Asp Ile  Leu Val Thr Glu Ile  Ala Glu Thr Asn Asn  Phe Ile Asn
    1550                 1555                 1560

Leu Ser  Phe Leu Arg Leu Phe  Arg Ala Ala Arg Leu  Ile Lys Leu
    1565                 1570                 1575

Leu Arg  Gln Gly Tyr Thr Ile  Arg Ile Leu Leu Trp  Thr Phe Val
    1580                 1585                 1590

Gln Ser  Phe Lys Ala Leu Pro  Tyr Val Cys Leu Leu  Ile Ala Met
    1595                 1600                 1605

Leu Phe  Phe Ile Tyr Ala Ile  Ile Gly Met Gln Val  Phe Gly Asn
    1610                 1615                 1620

Ile Ala  Leu Asp Asp Asp Thr  Ser Ile Asn Arg His  Asn Asn Phe
    1625                 1630                 1635

Arg Thr  Phe Leu Gln Ala Leu  Met Leu Leu Phe Arg  Ser Ala Thr
    1640                 1645                 1650

Gly Glu  Ala Trp His Glu Ile  Met Leu Ser Cys Leu  Ser Asn Gln
    1655                 1660                 1665

Ala Cys  Asp Glu Gln Ala Asn  Ala Thr Glu Cys Gly  Ser Asp Phe
    1670                 1675                 1680

Ala Tyr  Phe Tyr Phe Val Ser  Phe Ile Phe Leu Cys  Ser Phe Leu
    1685                 1690                 1695
```

```
Met Leu Asn Leu Phe Val Ala Val Ile Met Asp Asn Phe Glu Tyr
    1700                1705                1710

Leu Thr Arg Asp Ser Ser Ile Leu Gly Pro His His Leu Asp Glu
    1715                1720                1725

Phe Ile Arg Val Trp Ala Glu Tyr Asp Pro Ala Ala Cys Gly Arg
    1730                1735                1740

Ile Ser Tyr Asn Asp Met Phe Glu Met Leu Lys His Met Ser Pro
    1745                1750                1755

Pro Leu Gly Leu Gly Lys Lys Cys Pro Ala Arg Val Ala Tyr Lys
    1760                1765                1770

Arg Leu Val Arg Met Asn Met Pro Ile Ser Asn Glu Asp Met Thr
    1775                1780                1785

Val His Phe Thr Ser Thr Leu Met Ala Leu Ile Arg Thr Ala Leu
    1790                1795                1800

Glu Ile Lys Leu Ala Pro Ala Gly Thr Lys Gln His Gln Cys Asp
    1805                1810                1815

Ala Glu Leu Arg Lys Glu Ile Ser Val Val Trp Ala Asn Leu Pro
    1820                1825                1830

Gln Lys Thr Leu Asp Leu Leu Val Pro Pro His Lys Pro Asp Glu
    1835                1840                1845

Met Thr Val Gly Lys Val Tyr Ala Ala Leu Met Ile Phe Asp Phe
    1850                1855                1860

Tyr Lys Gln Asn Lys Thr Thr Arg Asp Gln Met Gln Gln Ala Pro
    1865                1870                1875

Gly Gly Leu Ser Gln Met Gly Pro Val Ser Leu Phe His Pro Leu
    1880                1885                1890

Lys Ala Thr Leu Glu Gln Thr Gln Pro Ala Val Leu Arg Gly Ala
    1895                1900                1905

Arg Val Phe Leu Arg Gln Lys Ser Ser Thr Ser Leu Ser Asn Gly
    1910                1915                1920

Gly Ala Ile Gln Asn Gln Glu Ser Gly Ile Lys Glu Ser Val Ser
    1925                1930                1935

Trp Gly Thr Gln Arg Thr Gln Asp Ala Pro His Glu Ala Arg Pro
    1940                1945                1950

Pro Leu Glu Arg Gly His Ser Thr Glu Ile Pro Val Gly Arg Ser
    1955                1960                1965

Gly Ala Leu Ala Val Asp Val Gln Met Gln Ser Ile Thr Arg Arg
    1970                1975                1980

Gly Pro Asp Gly Glu Pro Gln Pro Gly Leu Glu Ser Gln Gly Arg
    1985                1990                1995

Ala Ala Ser Met Pro Arg Leu Ala Ala Glu Thr Gln Pro Val Thr
    2000                2005                2010

Asp Ala Ser Pro Met Lys Arg Ser Ile Ser Thr Leu Ala Gln Arg
    2015                2020                2025

Pro Arg Gly Thr His Leu Cys Ser Thr Thr Pro Asp Arg Pro Pro
    2030                2035                2040

Pro Ser Gln Ala Ser Ser His His His His His Arg Cys His Arg
    2045                2050                2055

Arg Arg Asp Arg Lys Gln Arg Ser Leu Glu Lys Gly Pro Ser Leu
    2060                2065                2070

Ser Ala Asp Met Asp Gly Ala Pro Ser Ser Ala Val Gly Pro Gly
    2075                2080                2085

Leu Pro Pro Gly Glu Gly Pro Thr Gly Cys Arg Arg Glu Arg Glu
```

```
    2090                2095                2100

Arg Arg  Gln Glu Arg Gly Arg  Ser Gln Glu Arg Arg  Gln Pro Ser
    2105                2110                2115

Ser Ser  Ser Ser Glu Lys Gln  Arg Phe Tyr Ser Cys  Asp Arg Phe
    2120                2125                2130

Gly Gly  Arg Glu Pro Pro Lys  Pro Lys Pro Ser Leu  Ser Ser His
    2135                2140                2145

Pro Thr  Ser Pro Thr Ala Gly  Gln Glu Pro Gly Pro  His Pro Gln
    2150                2155                2160

Gly Ser  Gly Ser Val Asn Gly  Ser Pro Leu Leu Ser  Thr Ser Gly
    2165                2170                2175

Ala Ser  Thr Pro Gly Arg Gly  Gly Arg Arg Gln Leu  Pro Gln Thr
    2180                2185                2190

Pro Leu  Thr Pro Arg Pro Ser  Ile Thr Tyr Lys Thr  Ala Asn Ser
    2195                2200                2205

Ser Pro  Ile His Phe Ala Gly  Ala Gln Thr Ser Leu  Pro Ala Phe
    2210                2215                2220

Ser Pro  Gly Arg Leu Ser Arg  Gly Leu Ser Glu His  Asn Ala Leu
    2225                2230                2235

Leu Gln  Arg Asp Pro Leu Ser  Gln Pro Leu Ala Pro  Gly Ser Arg
    2240                2245                2250

Ile Gly  Ser Asp Pro Tyr Leu  Gly Gln Arg Leu Asp  Ser Glu Ala
    2255                2260                2265

Ser Val  His Ala Leu Pro Glu  Asp Thr Leu Thr Phe  Glu Glu Ala
    2270                2275                2280

Val Ala  Thr Asn Ser Gly Arg  Ser Ser Arg Thr Ser  Tyr Val Ser
    2285                2290                2295

Ser Leu  Thr Ser Gln Ser His  Pro Leu Arg Arg Val  Pro Asn Gly
    2300                2305                2310

Tyr His  Cys Thr Leu Gly Leu  Ser Ser Gly Gly Arg  Ala Arg His
    2315                2320                2325

Ser Tyr  His His Pro Asp Gln  Asp His Trp Cys
    2330                2335

<210> SEQ ID NO 3
<211> LENGTH: 6984
<212> TYPE: DNA
<213> ORGANISM: Mus musculus

<400> SEQUENCE: 3

atggtccgct tcggggacga gctaggcggc cgctatgggg gcaccggcgg cggggagcgg     60

gctcggggtg gcggggccgg cggggcgggt ggcccgggcc agggggggtct gccgccgggc    120

cagcgggtcc tgtacaagca gtccattgcg cagcgcgcac ggactatggc cctgtacaac    180

cccatcccag tcaagcagaa ctgcttcacc gtcaaccgct cgctcttcgt cttcagcgag    240

gacaacgtcg tccgcaaata cgctaagcgc atcaccgaat ggccgccctt cgaatacatg    300

atcctggcca ccatcatcgc caactgcatt gttctggccc tggagcagca cctccctgat    360

ggggacaaga ctcccatgtc tgagcgacta gatgacacgg agccttactt catcgggatc    420

ttttgcttcg aggcgggcat caagatcata gccctgggct ttgttttcca caagggctcc    480

taccttcgga acggctggaa tgtcatggac ttcgtggtgg tcctcacggg gattctcgcc    540

acagctggaa ctgactttga cctgcgcaca ctgagggctg tgcgtgtgct taggcccctg    600

aagctggtgt ctggaattcc aagcttgcag gtggtgctta agtccatcat gaaggccatg    660
```

```
gtcccgctgc tgcagattgg gctgctgctc ttctttgcca tcctcatgtt tgccatcatc    720
ggcctcgaat tctatatggg caaattccat aaggcctgtt tccccaacag cacagataca    780
gagcctgtgg gtgactttcc ctgtggcaaa gatccccctg ctcgtcagtg tgatggtgac    840
accgaatgcc gggagtactg gccaggaccc aactttggca tcaccaattt tgacaacatc    900
ctgtttgcca tcttgacagt gttccagtgt atcaccatgg agggctggac tgacatcctc    960
tacaatacaa atgatgcggc tggcaacaca tggaactggt tgtacttcat ccccctcatc   1020
atcattggct ccttcttcat gctcaacctg gtgctgggtg tgctttccgg agagtttgcc   1080
aaggagcggg agcgagtcga gaaccgccgc gccttcctga agctccgcag gcagcagcag   1140
attgagcgag agctgaatgg gtacttggag tggatcttca aggcagagga agtcatgttg   1200
gcagaggagg acaagaatgc agaagagaaa tccccttttgg atgtgttgaa gagagctgcc   1260
accaagaaga gccgaaatga cctcatccat gcagaagagg gggaggaccg gtttgtagac   1320
ctctgtgcag ttgggtctcc atttgctcgt gccagcctca agagtgggaa gacggagagc   1380
tcatcgtact tccggagaaa ggagaagatg ttccggttct ttatccggcg tatggtgaaa   1440
gcacagagct tctactgggt ggtactgtgt gtggtggccc tgaacacact gtgtgtggcc   1500
atggtgcact ataatcagcc tcagcggctt accactgcac tgtactttgc agagtttgtt   1560
ttcctgggtc tcttcctcac agagatgtcc ctgaagatgt atggcctagg gcccagaagt   1620
tacttcaggt cttccttcaa ctgctttgac tttggggtga ttgtggggag tatctttgaa   1680
gtagtctggg ctgccatcaa gccaggaacc tcctttggaa tcagtgtgct gcgggctctg   1740
cgactgctga ggatattcaa agttaccaag tattggaact ctctgaggaa cctggtggtt   1800
tccctcctca attccatgaa gtccatcatc agccttctct tcctgctttt cctcttcatc   1860
gtggtcttcg ctctgttggg gatgcagctg tttgggggac agttcaactt tcaagatgag   1920
actccaacca ccaatttga taccttccca gctgccatcc tcactgtctt tcagatcctg    1980
acaggagagg attggaatgc cgtaatgtat catgggattg agtcgcaagg tggagtcagc   2040
aaaggcatgt ttcttccttt ttacttcatc gtcctgacac tgtttggaaa ctacaccctg   2100
ctgaatgttt ttctggccat tgctgtggac aaccttgcca atgcccagga gttgaccaag   2160
gatgaagagg agatggaaga agcagccaat cagaaacttg ctcttcagaa ggccaaagaa   2220
gtagctgaag tcagccccat gtctgctgcc aatatctcca tcgctgccag gcagcagaac   2280
tcggccaagg cgcgctcagt atgggagcag cgggccagtc agctaaggct ccagaatctg   2340
cgtgccagct gtgaggcatt gtacagtgag atggaccctg aggagcgcct gcgttatgcc   2400
agcacgcgcc atgtgaggcc agacatgaag acacacatgg accgacccct agtggtggag   2460
cctggtcgag atggcttgcg gggacccgtt gggagcaagt caaagcctga aggcacggag   2520
gccacagaaa gcgcggacct acctcgcagg caccaccggc accgtgatag ggacaagacc   2580
tcagccacag cacctgctgg aggcgaacag gacaggacag aaagcaccga gaccggggcc   2640
cgggaggaac gtgcgcgccc tcgtcgaagt cacagcaagg agactccagg ggctgacacg   2700
caagtgcgct gtgagcgcag tagacgtcac caccggcgcg gctccccgga ggaggccact   2760
gaacgggagc ctcggcgcca ccgtgcccac cggcatgcac aggactcaag caaggagggc   2820
acggcgccgg tgcttgtacc caagggtgag cgacgagcaa gacaccgagg cccacgcacg   2880
ggtccacgtg aggcagagaa caacgaggag cccacacgca ggcaccgtgc aaggcataag   2940
gtgccaccca cactgcagcc cccagagagg gaggctgcag agaaggagag caacgcggtg   3000
```

-continued

```
gaaggggata aggaaacccg aaatcaccag cccaaggaac ctcactgtga cctggaggcc   3060
attgcagtta caggtgtggg ccctctgcac atgctgccca gcacctgtct ccagaaagtg   3120
gacgagcaac cagaggatgc agacaaccag cgtaatgtca cccggatggg cagtcagccc   3180
tcagatccca gcaccactgt gcatgtccca gtgacactga caggccctcc tggggagacc   3240
cctgtagttc ccagtggtaa catgaacctg gaaggccaag cagagggcaa gaaggaggca   3300
gaggcggatg atgtgctgag aagaggcccc aggcccatcg ttccctacag ctccatgttt   3360
tgtctcagcc ccaccaacct gcttcgtcgc ttctgccatt acattgtgac catgcggtac   3420
tttgagatgg taattcttgt ggtcattgcc ttgagcagca ttgccctggc tgcagaggat   3480
cctgtgcgga cagattcatt caggaacaac gctttaaagt acatggatta catctttaca   3540
ggagtcttca cctttgaaat ggtcataaag atgatagact tgggcttgct gctgcacccct  3600
ggtgcctact tccgggacct gtggaacatt ctggacttca ttgttgtcag tggagccctg   3660
gtggcatttg cgttctcgag cttcatggga ggatccaaag ggaaagacat caataccatc   3720
aagtctctga gagtcctgcg tgtcctgagg cccctcaaga ccatcaagcg gctgcctaag   3780
ctcaaggctg tctttgactg tgtggtgaac tccctgaaga acgtcttgaa catcctgatt   3840
gtctacatgc tcttcatgtt catatttgcc gtcattgccg tccagctctt caaagggaag   3900
ttcttttact gtactgatga atccaaggag ctggagaggg actgccgggg tcagtatttg   3960
gattatgaga aggaagaagt agaagcccag ccaaggcagt ggaagaaata tgacttccac   4020
tatgacaatg ttctctgggc cttgttgacg ctgttcacag tgtccacggg agaggggtgg   4080
cccatggtgc tgaaacactc tgtggatgcc acctatgagg aacaggggcc cagtcccggg   4140
ttccggatgg agctctccat cttctacgtg gtctactttg tggtcttccc tttttcttt    4200
gtcaacatct ttgtggcctt gatcattatc accttccagg aacagggaga taaggtgatg   4260
tctgaatgca gcttagaaaa gaatgagagg gcttgcattg attttgccat cagtgccaag   4320
cccctgacac ggtacatgcc tcaaaacaaa cagtcgttcc agtataagac atggacattc   4380
gtggtctctc caccctttga gtacttcatc atggctatga tagccctcaa cacagtggtg   4440
ctgatgatga agttctatga tgcaccttat gagtacgagc tgatgctgaa atgcctgaac   4500
attgtcttca catccatgtt ctcgatggag tgcatactga agatcatcgc ctttggggta   4560
ttgaactact tcagagatgc ctggaacgtc tttgactttg tcacggtttt gggaagtatt   4620
actgatattt tagtaacaga gatagcgaac aacttcatca acctaagctt ccttcgcctc   4680
ttccgggcgg cacggctgat caagctgctt cgccagggct acaccatccg catcctattg   4740
tggaccttcg tccagtcctt taaggcgctg ccctacgtgt gcctcctcat tgccatgctg   4800
ttcttcatct acgccatcat cggcatgcag gtttttggaa acattgccct tgatgatgac   4860
accagtatca accgacacaa caacttccgg acatttctgc aagccttaat gctattgttc   4920
aggagtgcca ctggggaggc ctggcatgag atcatgctgt cttgtctggg caaccgggcc   4980
tgtgacccac atgccaacgc cagtgagtgc gggagcgact ttgcctattt ttattttgtc   5040
tccttcatct tcctctgttc ctttctgatg ttgaacctct ttgttgctgt aatcatggac   5100
aattttgagt acctcactcg ggactcttcc atcctagggc ctcaccactt agacgaattc   5160
attcgagtct gggctgaata cgacccagct gcgtgtgggc gcatcagtta caatgacatg   5220
tttgagatgc tgaaacacat gtccccacct ctggggttgg ggaagaaatg cccggctcga   5280
gttgcataca agcgcctggt tcgcatgaac atgcccatat ccaatgagga catgacggtg   5340
cactttacgt ccacactgat ggccctcatc cggacagcac tggagatcaa gcttgcccca   5400
```

```
gcggggacga agcagcacca gtgtgatgct gagctgagaa aagagatctc ttctgtgtgg   5460
gctaatctgc cccagaagac tctggactta ctggtaccac cccacaaacc tgacgagatg   5520
acagtgggga aggtctatgc tgctctcatg atatttgact tctacaaaca gaacaaaacc   5580
accagagatc agactcacca agctcccgga ggcctgtccc agatgggtcc cgtttccctg   5640
ttccaccctc tgaaggccac cctggaacag acacagcccg ctgtgcttcg aggagctcgg   5700
gttttccttc ggcaaaagag tgcaacttcc ctcagcaatg ggggtgccat acaaacccag   5760
gaaagtggca tcaaggagtc gctgtcctgg ggcacgcaga ggacccaaga tgcactttat   5820
gaggccagag cacctctaga acgtggccat tctgcagaga tccctgtggg gcagtcagga   5880
acactggctg tggatgtcca gatgcagaac atgacactga gaggaccaga tggggagccc   5940
cagcctgggc tggaaagcca aggcagagct gcctctatgc cacgcctagc ggcagaaaca   6000
cagccggccc ctaatgccag ccccatgaag cgctccatct ccacactggc tccacgccca   6060
catgggactc agctttgcag cacagttctg gaccggcctc ctcctagcca ggcatcacat   6120
caccaccacc accgctgcca ccggcgcaga gacaagaagc aaaggtccct ggaaaagggg   6180
cccagcctgt ctgttgaccc agaaggtgca ccaagcactg ctgcaggacc tggtctgccc   6240
catggagaag gatccaccgc ctgccggcgg gaccgtaaac aggagcgagg ccggtcccag   6300
gagcggaggc agccctcatc ttcctcttca gagaagcagc gcttctattc ctgtgaccgc   6360
tttgggagcc gggagccccc gcaactgatg ccctcactca gtagccaccc cacatcgcca   6420
acagcggcgc tagagccagc accccaccca cagggcagtg gttccgttaa tgggagcccc   6480
ttgatgtcaa catccggtgc tagcaccccg ggccgaggtg ggcggaggca gctcccccag   6540
actcctctga ccccacgccc cagcatcacc tacaagaccg ccaattcctc gcctgtccac   6600
tttgctgagg gtcagagcgg cctcccagcc ttctcccctg gccgtctcag ccgcggcctt   6660
tctgaacaca atgccctgct ccagaaagag cccctgagcc agcctctagc tcctggctcc   6720
cgaattggct ctgaccctta cctagggcag cgtctggaca gtgaggcctc cgcccacacc   6780
ctgcctgagg atacactcac ctttgaagag gcagtggcca ccaactctgg ccgctcctcc   6840
aggacttcct atgtgtcctc cctcacttcc caatcccacc ctctccgccg tgtacccaat   6900
ggctatcact gcactttggg actcagcact ggcgtccggg cgcggcacag ctaccaccac   6960
cccgatcagg accactggtg ctag                                          6984
```

```
<210> SEQ ID NO 4
<211> LENGTH: 2327
<212> TYPE: PRT
<213> ORGANISM: Mus musculus

<400> SEQUENCE: 4

Met Val Arg Phe Gly Asp Glu Leu Gly Gly Arg Tyr Gly Gly Thr Gly
1               5                   10                  15

Gly Gly Glu Arg Ala Arg Gly Gly Gly Ala Gly Gly Ala Gly Gly Pro
            20                  25                  30

Gly Gln Gly Gly Leu Pro Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
```

-continued

```
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Thr Glu Pro Val Gly Asp Phe Pro Cys Gly Lys Asp Pro
            260                 265                 270

Pro Ala Arg Gln Cys Asp Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Lys Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Val Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Gln Arg Leu Thr Thr
            500                 505                 510
```

```
Ala Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Ile Phe Glu
545                 550                 555                 560

Val Val Trp Ala Ala Ile Lys Pro Gly Thr Ser Phe Gly Ile Ser Val
                565                 570                 575

Leu Arg Ala Leu Arg Leu Leu Arg Ile Phe Lys Val Thr Lys Tyr Trp
            580                 585                 590

Asn Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Tyr Ala
785                 790                 795                 800

Ser Thr Arg His Val Arg Pro Asp Met Lys Thr His Met Asp Arg Pro
                805                 810                 815

Leu Val Val Glu Pro Gly Arg Asp Gly Leu Arg Gly Pro Val Gly Ser
            820                 825                 830

Lys Ser Lys Pro Glu Gly Thr Glu Ala Thr Glu Ser Ala Asp Leu Pro
        835                 840                 845

Arg Arg His His Arg His Arg Asp Arg Asp Lys Thr Ser Ala Thr Ala
    850                 855                 860

Pro Ala Gly Gly Glu Gln Asp Arg Thr Glu Ser Thr Glu Thr Gly Ala
865                 870                 875                 880

Arg Glu Glu Arg Ala Arg Pro Arg Arg Ser His Ser Lys Glu Thr Pro
                885                 890                 895

Gly Ala Asp Thr Gln Val Arg Cys Glu Arg Ser Arg Arg His His Arg
            900                 905                 910

Arg Gly Ser Pro Glu Glu Ala Thr Glu Arg Glu Pro Arg Arg His Arg
        915                 920                 925
```

```
Ala His Arg His Ala Gln Asp Ser Ser Lys Glu Gly Thr Ala Pro Val
    930                 935                 940

Leu Val Pro Lys Gly Glu Arg Arg Ala Arg His Arg Gly Pro Arg Thr
945                 950                 955                 960

Gly Pro Arg Glu Ala Glu Asn Asn Glu Glu Pro Thr Arg Arg His Arg
                965                 970                 975

Ala Arg His Lys Val Pro Pro Thr Leu Gln Pro Pro Glu Arg Glu Ala
            980                 985                 990

Ala Glu Lys Glu Ser Asn Ala Val  Glu Gly Asp Lys Glu  Thr Arg Asn
        995                 1000                1005

His Gln  Pro Lys Glu Pro His  Cys Asp Leu Glu Ala  Ile Ala Val
    1010                 1015                 1020

Thr Gly  Val Gly Pro Leu His  Met Leu Pro Ser Thr  Cys Leu Gln
    1025                 1030                 1035

Lys Val  Asp Glu Gln Pro Glu  Asp Ala Asp Asn Gln  Arg Asn Val
    1040                 1045                 1050

Thr Arg  Met Gly Ser Gln Pro  Ser Asp Pro Ser Thr  Thr Val His
    1055                 1060                 1065

Val Pro  Val Thr Leu Thr Gly  Pro Pro Gly Glu Thr  Pro Val Val
    1070                 1075                 1080

Pro Ser  Gly Asn Met Asn Leu  Glu Gly Gln Ala Glu  Gly Lys Lys
    1085                 1090                 1095

Glu Ala  Glu Ala Asp Asp Val  Leu Arg Arg Gly Pro  Arg Pro Ile
    1100                 1105                 1110

Val Pro  Tyr Ser Ser Met Phe  Cys Leu Ser Pro Thr  Asn Leu Leu
    1115                 1120                 1125

Arg Arg  Phe Cys His Tyr Ile  Val Thr Met Arg Tyr  Phe Glu Met
    1130                 1135                 1140

Val Ile  Leu Val Val Ile Ala  Leu Ser Ser Ile Ala  Leu Ala Ala
    1145                 1150                 1155

Glu Asp  Pro Val Arg Thr Asp  Ser Phe Arg Asn Asn  Ala Leu Lys
    1160                 1165                 1170

Tyr Met  Asp Tyr Ile Phe Thr  Gly Val Phe Thr Phe  Glu Met Val
    1175                 1180                 1185

Ile Lys  Met Ile Asp Leu Gly  Leu Leu Leu His Pro  Gly Ala Tyr
    1190                 1195                 1200

Phe Arg  Asp Leu Trp Asn Ile  Leu Asp Phe Ile Val  Val Ser Gly
    1205                 1210                 1215

Ala Leu  Val Ala Phe Ala Phe  Ser Ser Phe Met Gly  Gly Ser Lys
    1220                 1225                 1230

Gly Lys  Asp Ile Asn Thr Ile  Lys Ser Leu Arg Val  Leu Arg Val
    1235                 1240                 1245

Leu Arg  Pro Leu Lys Thr Ile  Lys Arg Leu Pro Lys  Leu Lys Ala
    1250                 1255                 1260

Val Phe  Asp Cys Val Val Asn  Ser Leu Lys Asn Val  Leu Asn Ile
    1265                 1270                 1275

Leu Ile  Val Tyr Met Leu Phe  Met Phe Ile Phe Ala  Val Ile Ala
    1280                 1285                 1290

Val Gln  Leu Phe Lys Gly Lys  Phe Phe Tyr Cys Thr  Asp Glu Ser
    1295                 1300                 1305

Lys Glu  Leu Glu Arg Asp Cys  Arg Gly Gln Tyr Leu  Asp Tyr Glu
    1310                 1315                 1320

Lys Glu  Glu Val Glu Ala Gln  Pro Arg Gln Trp Lys  Lys Tyr Asp
```

-continued

```
    1325                1330                1335

Phe His  Tyr Asp Asn Val Leu  Trp Ala Leu Leu Thr  Leu Phe Thr
    1340                1345                1350

Val Ser  Thr Gly Glu Gly Trp  Pro Met Val Leu Lys  His Ser Val
    1355                1360                1365

Asp Ala  Thr Tyr Glu Glu Gln  Gly Pro Ser Pro Gly  Phe Arg Met
    1370                1375                1380

Glu Leu  Ser Ile Phe Tyr Val  Val Tyr Phe Val Val  Phe Pro Phe
    1385                1390                1395

Phe Phe  Val Asn Ile Phe Val  Ala Leu Ile Ile Ile  Thr Phe Gln
    1400                1405                1410

Glu Gln  Gly Asp Lys Val Met  Ser Glu Cys Ser Leu  Glu Lys Asn
    1415                1420                1425

Glu Arg  Ala Cys Ile Asp Phe  Ala Ile Ser Ala Lys  Pro Leu Thr
    1430                1435                1440

Arg Tyr  Met Pro Gln Asn Lys  Gln Ser Phe Gln Tyr  Lys Thr Trp
    1445                1450                1455

Thr Phe  Val Val Ser Pro Pro  Phe Glu Tyr Phe Ile  Met Ala Met
    1460                1465                1470

Ile Ala  Leu Asn Thr Val Val  Leu Met Met Lys Phe  Tyr Asp Ala
    1475                1480                1485

Pro Tyr  Glu Tyr Glu Leu Met  Leu Lys Cys Leu Asn  Ile Val Phe
    1490                1495                1500

Thr Ser  Met Phe Ser Met Glu  Cys Ile Leu Lys Ile  Ile Ala Phe
    1505                1510                1515

Gly Val  Leu Asn Tyr Phe Arg  Asp Ala Trp Asn Val  Phe Asp Phe
    1520                1525                1530

Val Thr  Val Leu Gly Ser Ile  Thr Asp Ile Leu Val  Thr Glu Ile
    1535                1540                1545

Ala Asn  Asn Phe Ile Asn Leu  Ser Phe Leu Arg Leu  Phe Arg Ala
    1550                1555                1560

Ala Arg  Leu Ile Lys Leu Leu  Arg Gln Gly Tyr Thr  Ile Arg Ile
    1565                1570                1575

Leu Leu  Trp Thr Phe Val Gln  Ser Phe Lys Ala Leu  Pro Tyr Val
    1580                1585                1590

Cys Leu  Leu Ile Ala Met Leu  Phe Phe Ile Tyr Ala  Ile Ile Gly
    1595                1600                1605

Met Gln  Val Phe Gly Asn Ile  Ala Leu Asp Asp Asp  Thr Ser Ile
    1610                1615                1620

Asn Arg  His Asn Asn Phe Arg  Thr Phe Leu Gln Ala  Leu Met Leu
    1625                1630                1635

Leu Phe  Arg Ser Ala Thr Gly  Glu Ala Trp His Glu  Ile Met Leu
    1640                1645                1650

Ser Cys  Leu Gly Asn Arg Ala  Cys Asp Pro His Ala  Asn Ala Ser
    1655                1660                1665

Glu Cys  Gly Ser Asp Phe Ala  Tyr Phe Tyr Phe Val  Ser Phe Ile
    1670                1675                1680

Phe Leu  Cys Ser Phe Leu Met  Leu Asn Leu Phe Val  Ala Val Ile
    1685                1690                1695

Met Asp  Asn Phe Glu Tyr Leu  Thr Arg Asp Ser Ser  Ile Leu Gly
    1700                1705                1710

Pro His  His Leu Asp Glu Phe  Ile Arg Val Trp Ala  Glu Tyr Asp
    1715                1720                1725
```

```
Pro Ala  Ala Cys Gly Arg Ile  Ser Tyr Asn Asp Met  Phe Glu Met
    1730                 1735                 1740

Leu Lys  His Met Ser Pro Pro  Leu Gly Leu Gly Lys  Lys Cys Pro
    1745                 1750                 1755

Ala Arg  Val Ala Tyr Lys Arg  Leu Val Arg Met Asn  Met Pro Ile
    1760                 1765                 1770

Ser Asn  Glu Asp Met Thr Val  His Phe Thr Ser Thr  Leu Met Ala
    1775                 1780                 1785

Leu Ile  Arg Thr Ala Leu Glu  Ile Lys Leu Ala Pro  Ala Gly Thr
    1790                 1795                 1800

Lys Gln  His Gln Cys Asp Ala  Glu Leu Arg Lys Glu  Ile Ser Ser
    1805                 1810                 1815

Val Trp  Ala Asn Leu Pro Gln  Lys Thr Leu Asp Leu  Leu Val Pro
    1820                 1825                 1830

Pro His  Lys Pro Asp Glu Met  Thr Val Gly Lys Val  Tyr Ala Ala
    1835                 1840                 1845

Leu Met  Ile Phe Asp Phe Tyr  Lys Gln Asn Lys Thr  Thr Arg Asp
    1850                 1855                 1860

Gln Thr  His Gln Ala Pro Gly  Gly Leu Ser Gln Met  Gly Pro Val
    1865                 1870                 1875

Ser Leu  Phe His Pro Leu Lys  Ala Thr Leu Glu Gln  Thr Gln Pro
    1880                 1885                 1890

Ala Val  Leu Arg Gly Ala Arg  Val Phe Leu Arg Gln  Lys Ser Ala
    1895                 1900                 1905

Thr Ser  Leu Ser Asn Gly Gly  Ala Ile Gln Thr Gln  Glu Ser Gly
    1910                 1915                 1920

Ile Lys  Glu Ser Leu Ser Trp  Gly Thr Gln Arg Thr  Gln Asp Ala
    1925                 1930                 1935

Leu Tyr  Glu Ala Arg Ala Pro  Leu Glu Arg Gly His  Ser Ala Glu
    1940                 1945                 1950

Ile Pro  Val Gly Gln Ser Gly  Thr Leu Ala Val Asp  Val Gln Met
    1955                 1960                 1965

Gln Asn  Met Thr Leu Arg Gly  Pro Asp Gly Glu Pro  Gln Pro Gly
    1970                 1975                 1980

Leu Glu  Ser Gln Gly Arg Ala  Ala Ser Met Pro Arg  Leu Ala Ala
    1985                 1990                 1995

Glu Thr  Gln Pro Ala Pro Asn  Ala Ser Pro Met Lys  Arg Ser Ile
    2000                 2005                 2010

Ser Thr  Leu Ala Pro Arg Pro  His Gly Thr Gln Leu  Cys Ser Thr
    2015                 2020                 2025

Val Leu  Asp Arg Pro Pro Pro  Ser Gln Ala Ser His  His His His
    2030                 2035                 2040

His Arg  Cys His Arg Arg Arg  Asp Lys Lys Gln Arg  Ser Leu Glu
    2045                 2050                 2055

Lys Gly  Pro Ser Leu Ser Val  Asp Pro Glu Gly Ala  Pro Ser Thr
    2060                 2065                 2070

Ala Ala  Gly Pro Gly Leu Pro  His Gly Glu Gly Ser  Thr Ala Cys
    2075                 2080                 2085

Arg Arg  Asp Arg Lys Gln Glu  Arg Gly Arg Ser Gln  Glu Arg Arg
    2090                 2095                 2100

Gln Pro  Ser Ser Ser Ser Ser  Glu Lys Gln Arg Phe  Tyr Ser Cys
    2105                 2110                 2115
```

```
Asp Arg  Phe Gly Ser Arg Glu  Pro Pro Gln Leu Met  Pro Ser Leu
    2120                 2125                 2130

Ser Ser  His Pro Thr Ser Pro  Thr Ala Ala Leu Glu  Pro Ala Pro
    2135                 2140                 2145

His Pro  Gln Gly Ser Gly Ser  Val Asn Gly Ser Pro  Leu Met Ser
    2150                 2155                 2160

Thr Ser  Gly Ala Ser Thr Pro  Gly Arg Gly Gly Arg  Arg Gln Leu
    2165                 2170                 2175

Pro Gln  Thr Pro Leu Thr Pro  Arg Pro Ser Ile Thr  Tyr Lys Thr
    2180                 2185                 2190

Ala Asn  Ser Ser Pro Val His  Phe Ala Glu Gly Gln  Ser Gly Leu
    2195                 2200                 2205

Pro Ala  Phe Ser Pro Gly Arg  Leu Ser Arg Gly Leu  Ser Glu His
    2210                 2215                 2220

Asn Ala  Leu Leu Gln Lys Glu  Pro Leu Ser Gln Pro  Leu Ala Pro
    2225                 2230                 2235

Gly Ser  Arg Ile Gly Ser Asp  Pro Tyr Leu Gly Gln  Arg Leu Asp
    2240                 2245                 2250

Ser Glu  Ala Ser Ala His Thr  Leu Pro Glu Asp Thr  Leu Thr Phe
    2255                 2260                 2265

Glu Glu  Ala Val Ala Thr Asn  Ser Gly Arg Ser Ser  Arg Thr Ser
    2270                 2275                 2280

Tyr Val  Ser Ser Leu Thr Ser  Gln Ser His Pro Leu  Arg Arg Val
    2285                 2290                 2295

Pro Asn  Gly Tyr His Cys Thr  Leu Gly Leu Ser Thr  Gly Val Arg
    2300                 2305                 2310

Ala Arg  His Ser Tyr His His  Pro Asp Gln Asp His  Trp Cys
    2315                 2320                 2325
```

<210> SEQ ID NO 5
<211> LENGTH: 7065
<212> TYPE: DNA
<213> ORGANISM: Rattus norvegicus

<400> SEQUENCE: 5

```
atggtccgct tcggggacga gctaggcggc cgctatgggg gcaccggcgg cggggagcgg     60

gctcggggcg gcggggccgg cggggccggt ggcccgggcc agggggggtct gccgccgggc    120

cagcgggtcc tgtacaagca gtccattgcg caacgcgcac ggaccatggc cctgtacaac    180

cccatcccag tcaagcagaa ctgcttcacc gtcaaccgct cgctcttcgt cttcagcgag    240

gacaacgtcg tccgcaaata tgctaagcgc atcaccgaat ggccgccctt cgaatatatg    300

atcctggcca ccatcatcgc caactgtatt gtcctggccc tggagcagca cctccctgat    360

ggggacaaga ctcccatgtc tgaacgactg gatgacacgg aaccttactt catcggcatc    420

ttttgcttcg aggcgggcat caagatcata gctctgggct tcgtgttcca caaaggctcc    480

tacctccgga atggctggaa cgtcatggac ttcgtggtgg tcctcacagg gattcttgcc    540

acagctggaa ctgactttga tctgcgcacc ctgagggctg tgcgtgtgct taggcccctg    600

aagttggtgt ctggaattcc aagcttgcag gtggtgctca agtccatcat gaaggccatg    660

gtcccgctgc tgcagatcgg gctgctgctc ttcttcgcca tcctcatgtt cgctatcatc    720

ggcctcgagt tctatatggg caaattccat aaggcctgct tccccaacag cacagatgca    780

gagcctgtgg gtgactttcc ttgtggcaag gaggcccctg ctcgtctgtg tgacagtgac    840

accgaatgcc gggagtactg gccaggaccc aactttggca tcaccaattt tgacaacatc    900
```

-continued

```
ctgtttgcca tcttgaccgt gttccagtgt atcaccatgg agggctggac tgacatcctc    960
tacaatacaa atgatgcggc cggcaacacg tggaactggt tgtacttcat ccccctcatc   1020
atcattggct ccttcttcat gctcaacctg gtgctcggtg tgctttcagg agagtttgcc   1080
aaagagcggg agcgagtcga gaaccgccgt gccttcctga agctccgcag gcagcagcag   1140
attgagcgag aactgaatgg gtacttggag tggatcttca aggcggagga agtcatgttg   1200
gcagaggagg acaagaacgc agaagagaag tccccttggg atgcagtgtt gaagagagct   1260
gctaccaaga agagccgaaa tgacctcatc catgcagaag agggggagga ccggtttgta   1320
gacctctgtg ctgctgggtc tccctttgct cgtgccagcc tcaagagtgg gaagacagag   1380
agctcatcgt acttccggag gaaggagaag atgttccggt tccttatccg tcgtatggtg   1440
aaagcacaga gcttctactg ggtggtactg tgcgtggtgg ccctgaacac gttgtgtgtg   1500
gccatggtac actataatca gcctcagcgg cttaccactg cactgtactt tgcagagttt   1560
gttttcctgg gtctcttcct cacagagatg tccctgaaga tgtacggtct agggcccaga   1620
agctacttcc ggtcttcctt caactgcttt gactttgggg tgattgtggg gagtatcttt   1680
gaagtagtct gggctgccat caagccagga acctccttcg gaatcagtgt gctgcgggct   1740
ctccgactgc tgaggatttt caaagtcacc aagtattgga actccctgag gaacctggtt   1800
gtttccctcc tcaactccat gaagtccatc atcagccttc tcttcctgct tttccttttc   1860
attgtggtct tcgctctgtt ggggatgcag ctgtttgggg gacagttcaa ctttcaagat   1920
gagactccaa ccaccaattt tgataccttc ccagctgcca tcctcactgt gtttcagatt   1980
ctgacaggag aggactggaa tgcagtcatg tatcatggga ttgagtcaca aggaggagtc   2040
agcaaaggca tgttttcatc cttttacttc atcgtcctga cactgtttgg aaactacacc   2100
ctgttgaacg ttttcttggc cattgctgtg gacaaccttg ccaatgccca ggagttgacc   2160
aaggatgaag aggagatgga agaggcagcc aatcagaagc ttgctcttca gaaggccaaa   2220
gaagtagctg aagtcagccc catgtctgct gccaacatct ccattgctgc ttttgtaaag   2280
caaactcgag gtactgtatc tcgcagctca tctgtctcca gcgtaaactc accgcagcag   2340
aactcggcca aggcgcgctc agtatgggag cagcgggcca gtcagctaag gctccagaac   2400
ctgcgtgcca gctgtgaggc actgtacagt gagatggacc cggaggagcg cctgcgttat   2460
gccagcacgc gccacgtgag gccagacatg aagacacaca tggaccgacc cctagtggtg   2520
gaacctggtc gggatggcct gcggggaccc gccgggaaca agtcaaagcc tgagggcacg   2580
gaggccaccg aaggtgcgga tccaccacgc cgacaccacc ggcatcgtga tagggacaag   2640
acctcagcct caacccctgc tggaggcgaa caggacagga cagactgccc aaaggccgaa   2700
agcaccgaga ccggggcccg ggaggaacgt gcgcgccctc gtcgaagtca cagcaaggag   2760
gctccagggg ctgacacaca agtgcgttgt gagcgcagta gacgtcacca ccggcgcgga   2820
tccccggagg aggccactga acgggaacct cggcgccacc gtgcccaccg gcacgcacag   2880
gactcaagca aggaaggcaa ggagggcact gcaccggtgc ttgtacccaa gggcgagcgt   2940
cgcgcaagac atcgaggccc gcgtacgggc cccccgtgaga cagagaacag tgaggagccc   3000
acacgcaggc accgtgcaaa gcataaggtg ccaccaacac ttgagccccc agagagggag   3060
gttgcagaga aggagagcaa cgtggtggaa ggggataagg aaactcgaaa tcaccagccc   3120
aaggaacctc gctgtgacct ggaggccatt gcggttacag gcgtgggctc tctgcacatg   3180
ctgcccagca cctgtctcca gaaagtggac gaacagccag aggatgcaga caaccagcgt   3240
```

```
aatgtcaccc ggatgggcag tcagccctca gaccccagca ccactgtgca tgtcccagtg   3300
acactgacag gccctcccgg ggaggccact gtagttccca gtgctaacac ggacctggaa   3360
ggccaagcgg agggcaagaa ggaggcagag gctgacgatg tgctgagaag aggccccagg   3420
cccatcgttc cctacagttc catgttctgc ctcagcccca ccaacctact ccgtcgcttc   3480
tgccattaca ttgtgaccat gcggtacttt gagatggtga ttcttgtggt catcgccttg   3540
agcagcattg ccctggctgc tgaggatccc gtgcggaccg actcattccg gaacaatgct   3600
ctgaagtaca tggactacat ctttacagga gtcttcacct ttgagatggt cataaagatg   3660
atagacttgg gcctgctgct gcaccctggg gcctacttcc gggacctgtg gaacattctg   3720
gacttcattg ttgtcagtgg agccctggtg gcatttgcat tctcaggatc caaagggaaa   3780
gacatcaata ccatcaagtc tctgagagtc ctgcgagtcc tgcggcccct caagaccatc   3840
aagcggctgc ctaaactcaa ggctgtgttt gactgtgtgg tgaactctct gaagaatgtc   3900
ttgaacatcc tgatcgtcta catgctcttc atgtttatat ttgccgtcat cgccgtccaa   3960
ctcttcaaag ggaagttctt ttactgcact gatgagtcca aggagctgga gcgggactgc   4020
aggggtcagt atttggatta tgagaaggaa gaggtagaag cccagccaag gcagtggaag   4080
aaatatgact tccactatga caatgtgctc tgggccttgc tgactctgtt tacggtgtcc   4140
acaggagagg ggtggcccat ggtgctgaaa cactctgtgg acgccaccta tgaggagcag   4200
gggccaagcc ccgggtttcg gatggagctt tccatcttct atgtggtcta ctttgtggtc   4260
ttcccttttt tctttgtcaa catctttgtg gccttgatca tcatcacctt ccaggagcag   4320
ggggacaagg tgatgtctga gtgcagtctg gaaaagaatg agagggcttg cattgacttt   4380
gccatcagcg ccaaacccct gacacggtac atgcctcaga acaagcagtc gttccagtat   4440
aagacatgga catttgtggt ctctccaccc tttgagtact tcattatggc catgatagcc   4500
ctcaacacag tggtgctgat gatgaagttc tacgatgccc cttatgagta cgagctgatg   4560
ctgaagtgct tgaacatcgt cttcacatcc atgttctctc tggagtgcat cctgaagatc   4620
atcgccttcg ggtgttgaa ctacttcaga gatgcctgga acgtctttga ctttgtcact   4680
gttttgggaa gtattactga tattttagta acggagattg cggaaacgaa caacttcatc   4740
aacttgagct tccttcgcct cttccgggca gcacggctga tcaagctgct tcgccagggc   4800
tacaccatcc gcatcttgtt atggaccttt gtccagtcct ttaaggcgct gccctacgtg   4860
tgcctcctca ttgccatgct gttcttcatc tacgccatca tcggcatgca ggtttttgga   4920
aacattgccc ttgatgatgg caccagcatc aaccgacaca acaacttccg gacatttctg   4980
caagccttaa tgctgttgtt caggagtgcc actggggagg cctggcacga aatcatgctg   5040
tcttgcctgg gcaaccgggc ctgcgaccca catgccaacg ccagcgaatg cgggagcgac   5100
tttgcctatt tttattttgt ctccttcatc ttcctctgtt cctttctgat gctgaacctc   5160
tttgttgctg tgatcatgga caatttcgaa tacctcacgc gggattcttc catcctaggg   5220
ccgcaccacc tcgatgaatt cattcgcgtc tgggctgaat acgacccagc tgcgtgtggg   5280
cgcatcagtt acaatgacat gtttgagatg ctgaaacaca tgtccccacc tctgggtttg   5340
gggaagaaat gcccggctcg agttgcatac aagcgcctgg ttcgaatgaa catgcccata   5400
tccaatgagg acatgacggt acactttaca tccacactga tggccctcat ccggacggca   5460
ctggagatca agcttgcccc agcggggaca aaacagcacc aatgtgatgc tgagctgagg   5520
aaggagatct cttctgtgtg ggctaatctg ccccagaaga ctctggactt actggtgcca   5580
ccccacaaac ctgacgagat gacagtgggg aaggtctatg cggctctcat gatatttgac   5640
```

```
ttctacaaac agaacaaaac caccagagat cagactcacc aagctcctgg aggcctgtcc   5700

cagatgggtc ctgtttccct gttccatcct ctgaaggcca ccctggagca gacacagccc   5760

gctgtgctcc gaggagctcg ggttttcctt cgacaaaaga gtgcaacttc cctcagcaat   5820

gggggcgcca tacaaaccca ggaaagtggc atcaaggagt ccctgtcctg ggcacgcag    5880

aggacccagg acgtacttta tgaggccaga gcacctctag aacgtggcca ttctgcagag   5940

atccctgtgg ggcagccagg agcactggct gtagatgtcc agatgcagaa catgacattg   6000

agaggaccgg atggggagcc ccagcctggc ctggagagcc aaggccgagc ggcctctatg   6060

ccacgcctgg cggcagaaac acagccggcc cctaatgcca gccccatgaa gcgctccatc   6120

tccacactgg ctccacgccc gcatgggact cagctttgca acacagtcct ggaccggcca   6180

cctcctagcc aggtgtccca tcaccaccac caccgctgcc accggcgcag ggacaagaag   6240

cagaggtccc tggaaaaggg gcccagcctg tctgttgaca cagaaggtgc accaagtact   6300

gctgcaggat ctggcctgcc ccatggagaa gggtccacag gctgccggcg ggagcgtaag   6360

caagagcgag gccggtccca ggagcggagg cagccctcct cctcttcttc agagaagcag   6420

cgcttctatt cctgtgaccg ctttgggagc cgggagcccc cacaacctaa gccctccctc   6480

agtagccacc ccatatcgcc aacagcggca ctagagccag gaccccaccc gcagggcagt   6540

ggttccgtta atgggagccc cttgatgtca acatctggtg ctagcacgcc gggccgaggt   6600

gggcggaggc agctccccca gactcccctg accccacgcc ccagcatcac ctacaagacg   6660

gccaattcct cgcctgtcca ctttgctgag ggtcagagtg gccttccagc cttctcccct   6720

ggccgtctca gccgcggcct ttctgaacac aatgccctgc tccagaaaga gcccctgagc   6780

cagcctctag cttctggctc ccgcattggc tctgaccctt acctagggca gcgtctggac   6840

agtgaggcct ctgcccacaa cctgcctgag gatacactca cctttgaaga ggccgtggcc   6900

accaactctg gccgctcctc caggacttcc tatgtgtcct ccctcacttc ccaatcccac   6960

cctctccgcc gtgtacccaa tggctaccac tgcactttgg gactcagcac cggcgtccgg   7020

gcgcggcaca gctaccacca cccagaccag gatcactggt gctag                   7065
```

```
<210> SEQ ID NO 6
<211> LENGTH: 2354
<212> TYPE: PRT
<213> ORGANISM: Rattus norvegicus

<400> SEQUENCE: 6

Met Val Arg Phe Gly Asp Glu Leu Gly Gly Arg Tyr Gly Gly Thr Gly
1               5                   10                  15

Gly Gly Glu Arg Ala Arg Gly Gly Gly Ala Gly Gly Ala Gly Gly Pro
            20                  25                  30

Gly Gln Gly Gly Leu Pro Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
```

```
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Asp Ser Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Lys Asn Ala Glu Glu Lys Ser Pro Leu Asp Ala Val
                405                 410                 415

Leu Lys Arg Ala Ala Thr Lys Lys Ser Arg Asn Asp Leu Ile His Ala
            420                 425                 430

Glu Glu Gly Glu Asp Arg Phe Val Asp Leu Cys Ala Ala Gly Ser Pro
        435                 440                 445

Phe Ala Arg Ala Ser Leu Lys Ser Gly Lys Thr Glu Ser Ser Ser Tyr
    450                 455                 460

Phe Arg Arg Lys Glu Lys Met Phe Arg Phe Leu Ile Arg Arg Met Val
465                 470                 475                 480

Lys Ala Gln Ser Phe Tyr Trp Val Val Leu Cys Val Val Ala Leu Asn
                485                 490                 495

Thr Leu Cys Val Ala Met Val His Tyr Asn Gln Pro Gln Arg Leu Thr
            500                 505                 510

Thr Ala Leu Tyr Phe Ala Glu Phe Val Phe Leu Gly Leu Phe Leu Thr
        515                 520                 525

Glu Met Ser Leu Lys Met Tyr Gly Leu Gly Pro Arg Ser Tyr Phe Arg
    530                 535                 540
```

```
Ser Ser Phe Asn Cys Phe Asp Phe Gly Val Ile Val Gly Ser Ile Phe
545                 550                 555                 560

Glu Val Val Trp Ala Ala Ile Lys Pro Gly Thr Ser Phe Gly Ile Ser
                565                 570                 575

Val Leu Arg Ala Leu Arg Leu Leu Arg Ile Phe Lys Val Thr Lys Tyr
            580                 585                 590

Trp Asn Ser Leu Arg Asn Leu Val Val Ser Leu Leu Asn Ser Met Lys
        595                 600                 605

Ser Ile Ile Ser Leu Leu Phe Leu Leu Phe Leu Phe Ile Val Val Phe
    610                 615                 620

Ala Leu Leu Gly Met Gln Leu Phe Gly Gly Gln Phe Asn Phe Gln Asp
625                 630                 635                 640

Glu Thr Pro Thr Thr Asn Phe Asp Thr Phe Pro Ala Ala Ile Leu Thr
                645                 650                 655

Val Phe Gln Ile Leu Thr Gly Glu Asp Trp Asn Ala Val Met Tyr His
            660                 665                 670

Gly Ile Glu Ser Gln Gly Gly Val Ser Lys Gly Met Phe Ser Ser Phe
        675                 680                 685

Tyr Phe Ile Val Leu Thr Leu Phe Gly Asn Tyr Thr Leu Leu Asn Val
    690                 695                 700

Phe Leu Ala Ile Ala Val Asp Asn Leu Ala Asn Ala Gln Glu Leu Thr
705                 710                 715                 720

Lys Asp Glu Glu Glu Met Glu Glu Ala Ala Asn Gln Lys Leu Ala Leu
                725                 730                 735

Gln Lys Ala Lys Glu Val Ala Glu Val Ser Pro Met Ser Ala Ala Asn
            740                 745                 750

Ile Ser Ile Ala Ala Phe Val Lys Gln Thr Arg Gly Thr Val Ser Arg
        755                 760                 765

Ser Ser Ser Val Ser Ser Val Asn Ser Pro Gln Gln Asn Ser Ala Lys
    770                 775                 780

Ala Arg Ser Val Trp Glu Gln Arg Ala Ser Gln Leu Arg Leu Gln Asn
785                 790                 795                 800

Leu Arg Ala Ser Cys Glu Ala Leu Tyr Ser Glu Met Asp Pro Glu Glu
                805                 810                 815

Arg Leu Arg Tyr Ala Ser Thr Arg His Val Arg Pro Asp Met Lys Thr
            820                 825                 830

His Met Asp Arg Pro Leu Val Val Glu Pro Gly Arg Asp Gly Leu Arg
        835                 840                 845

Gly Pro Ala Gly Asn Lys Ser Lys Pro Glu Gly Thr Glu Ala Thr Glu
    850                 855                 860

Gly Ala Asp Pro Pro Arg Arg His His Arg His Arg Asp Arg Asp Lys
865                 870                 875                 880

Thr Ser Ala Ser Thr Pro Ala Gly Gly Glu Gln Asp Arg Thr Asp Cys
                885                 890                 895

Pro Lys Ala Glu Ser Thr Glu Thr Gly Ala Arg Glu Glu Arg Ala Arg
            900                 905                 910

Pro Arg Arg Ser His Ser Lys Glu Ala Pro Gly Ala Asp Thr Gln Val
        915                 920                 925

Arg Cys Glu Arg Ser Arg Arg His His Arg Arg Gly Ser Pro Glu Glu
    930                 935                 940

Ala Thr Glu Arg Glu Pro Arg Arg His Arg Ala His Arg His Ala Gln
945                 950                 955                 960
```

```
Asp Ser Ser Lys Glu Gly Lys Glu Gly Thr Ala Pro Val Leu Val Pro
                965                 970                 975

Lys Gly Glu Arg Arg Ala Arg His Arg Gly Pro Arg Thr Gly Pro Arg
            980                 985                 990

Glu Thr Glu Asn Ser Glu Glu Pro  Thr Arg Arg His Arg  Ala Lys His
        995                 1000                 1005

Lys Val  Pro Pro Thr Leu Glu  Pro Pro Glu Arg Glu  Val Ala Glu
    1010                 1015                 1020

Lys Glu  Ser Asn Val Val Glu  Gly Asp Lys Glu Thr  Arg Asn His
    1025                 1030                 1035

Gln Pro  Lys Glu Pro Arg Cys  Asp Leu Glu Ala Ile  Ala Val Thr
    1040                 1045                 1050

Gly Val  Gly Ser Leu His Met  Leu Pro Ser Thr Cys  Leu Gln Lys
    1055                 1060                 1065

Val Asp  Glu Gln Pro Glu Asp  Ala Asp Asn Gln Arg  Asn Val Thr
    1070                 1075                 1080

Arg Met  Gly Ser Gln Pro Ser  Asp Pro Ser Thr Thr  Val His Val
    1085                 1090                 1095

Pro Val  Thr Leu Thr Gly Pro  Pro Gly Glu Ala Thr  Val Val Pro
    1100                 1105                 1110

Ser Ala  Asn Thr Asp Leu Glu  Gly Gln Ala Glu Gly  Lys Lys Glu
    1115                 1120                 1125

Ala Glu  Ala Asp Asp Val Leu  Arg Arg Gly Pro Arg  Pro Ile Val
    1130                 1135                 1140

Pro Tyr  Ser Ser Met Phe Cys  Leu Ser Pro Thr Asn  Leu Leu Arg
    1145                 1150                 1155

Arg Phe  Cys His Tyr Ile Val  Thr Met Arg Tyr Phe  Glu Met Val
    1160                 1165                 1170

Ile Leu  Val Val Ile Ala Leu  Ser Ser Ile Ala Leu  Ala Ala Glu
    1175                 1180                 1185

Asp Pro  Val Arg Thr Asp Ser  Phe Arg Asn Asn Ala  Leu Lys Tyr
    1190                 1195                 1200

Met Asp  Tyr Ile Phe Thr Gly  Val Phe Thr Phe Glu  Met Val Ile
    1205                 1210                 1215

Lys Met  Ile Asp Leu Gly Leu  Leu Leu His Pro Gly  Ala Tyr Phe
    1220                 1225                 1230

Arg Asp  Leu Trp Asn Ile Leu  Asp Phe Ile Val Val  Ser Gly Ala
    1235                 1240                 1245

Leu Val  Ala Phe Ala Phe Ser  Gly Ser Lys Gly Lys  Asp Ile Asn
    1250                 1255                 1260

Thr Ile  Lys Ser Leu Arg Val  Leu Arg Val Leu Arg  Pro Leu Lys
    1265                 1270                 1275

Thr Ile  Lys Arg Leu Pro Lys  Leu Lys Ala Val Phe  Asp Cys Val
    1280                 1285                 1290

Val Asn  Ser Leu Lys Asn Val  Leu Asn Ile Leu Ile  Val Tyr Met
    1295                 1300                 1305

Leu Phe  Met Phe Ile Phe Ala  Val Ile Ala Val Gln  Leu Phe Lys
    1310                 1315                 1320

Gly Lys  Phe Phe Tyr Cys Thr  Asp Glu Ser Lys Glu  Leu Glu Arg
    1325                 1330                 1335

Asp Cys  Arg Gly Gln Tyr Leu  Asp Tyr Glu Lys Glu  Glu Val Glu
    1340                 1345                 1350

Ala Gln  Pro Arg Gln Trp Lys  Lys Tyr Asp Phe His  Tyr Asp Asn
```

```
    1355                1360                1365

Val Leu  Trp Ala Leu Leu Thr  Leu Phe Thr Val Ser  Thr Gly Glu
    1370                1375                1380

Gly Trp  Pro Met Val Leu Lys  His Ser Val Asp Ala  Thr Tyr Glu
    1385                1390                1395

Glu Gln  Gly Pro Ser Pro Gly  Phe Arg Met Glu Leu  Ser Ile Phe
    1400                1405                1410

Tyr Val  Val Tyr Phe Val Val  Phe Pro Phe Phe Phe  Val Asn Ile
    1415                1420                1425

Phe Val  Ala Leu Ile Ile Ile  Thr Phe Gln Glu Gln  Gly Asp Lys
    1430                1435                1440

Val Met  Ser Glu Cys Ser Leu  Glu Lys Asn Glu Arg  Ala Cys Ile
    1445                1450                1455

Asp Phe  Ala Ile Ser Ala Lys  Pro Leu Thr Arg Tyr  Met Pro Gln
    1460                1465                1470

Asn Lys  Gln Ser Phe Gln Tyr  Lys Thr Trp Thr Phe  Val Val Ser
    1475                1480                1485

Pro Pro  Phe Glu Tyr Phe Ile  Met Ala Met Ile Ala  Leu Asn Thr
    1490                1495                1500

Val Val  Leu Met Met Lys Phe  Tyr Asp Ala Pro Tyr  Glu Tyr Glu
    1505                1510                1515

Leu Met  Leu Lys Cys Leu Asn  Ile Val Phe Thr Ser  Met Phe Ser
    1520                1525                1530

Leu Glu  Cys Ile Leu Lys Ile  Ile Ala Phe Gly Val  Leu Asn Tyr
    1535                1540                1545

Phe Arg  Asp Ala Trp Asn Val  Phe Asp Phe Val Thr  Val Leu Gly
    1550                1555                1560

Ser Ile  Thr Asp Ile Leu Val  Thr Glu Ile Ala Glu  Thr Asn Asn
    1565                1570                1575

Phe Ile  Asn Leu Ser Phe Leu  Arg Leu Phe Arg Ala  Ala Arg Leu
    1580                1585                1590

Ile Lys  Leu Leu Arg Gln Gly  Tyr Thr Ile Arg Ile  Leu Leu Trp
    1595                1600                1605

Thr Phe  Val Gln Ser Phe Lys  Ala Leu Pro Tyr Val  Cys Leu Leu
    1610                1615                1620

Ile Ala  Met Leu Phe Phe Ile  Tyr Ala Ile Ile Gly  Met Gln Val
    1625                1630                1635

Phe Gly  Asn Ile Ala Leu Asp  Asp Gly Thr Ser Ile  Asn Arg His
    1640                1645                1650

Asn Asn  Phe Arg Thr Phe Leu  Gln Ala Leu Met Leu  Leu Phe Arg
    1655                1660                1665

Ser Ala  Thr Gly Glu Ala Trp  His Glu Ile Met Leu  Ser Cys Leu
    1670                1675                1680

Gly Asn  Arg Ala Cys Asp Pro  His Ala Asn Ala Ser  Glu Cys Gly
    1685                1690                1695

Ser Asp  Phe Ala Tyr Phe Tyr  Phe Val Ser Phe Ile  Phe Leu Cys
    1700                1705                1710

Ser Phe  Leu Met Leu Asn Leu  Phe Val Ala Val Ile  Met Asp Asn
    1715                1720                1725

Phe Glu  Tyr Leu Thr Arg Asp  Ser Ser Ile Leu Gly  Pro His His
    1730                1735                1740

Leu Asp  Glu Phe Ile Arg Val  Trp Ala Glu Tyr Asp  Pro Ala Ala
    1745                1750                1755
```

```
Cys Gly  Arg Ile Ser Tyr Asn  Asp Met Phe Glu Met  Leu Lys His
    1760                 1765                 1770

Met Ser  Pro Pro Leu Gly Leu  Gly Lys Lys Cys Pro  Ala Arg Val
    1775                 1780                 1785

Ala Tyr  Lys Arg Leu Val Arg  Met Asn Met Pro Ile  Ser Asn Glu
    1790                 1795                 1800

Asp Met  Thr Val His Phe Thr  Ser Thr Leu Met Ala  Leu Ile Arg
    1805                 1810                 1815

Thr Ala  Leu Glu Ile Lys Leu  Ala Pro Ala Gly Thr  Lys Gln His
    1820                 1825                 1830

Gln Cys  Asp Ala Glu Leu Arg  Lys Glu Ile Ser Ser  Val Trp Ala
    1835                 1840                 1845

Asn Leu  Pro Gln Lys Thr Leu  Asp Leu Leu Val Pro  Pro His Lys
    1850                 1855                 1860

Pro Asp  Glu Met Thr Val Gly  Lys Val Tyr Ala Ala  Leu Met Ile
    1865                 1870                 1875

Phe Asp  Phe Tyr Lys Gln Asn  Lys Thr Thr Arg Asp  Gln Thr His
    1880                 1885                 1890

Gln Ala  Pro Gly Gly Leu Ser  Gln Met Gly Pro Val  Ser Leu Phe
    1895                 1900                 1905

His Pro  Leu Lys Ala Thr Leu  Glu Gln Thr Gln Pro  Ala Val Leu
    1910                 1915                 1920

Arg Gly  Ala Arg Val Phe Leu  Arg Gln Lys Ser Ala  Thr Ser Leu
    1925                 1930                 1935

Ser Asn  Gly Gly Ala Ile Gln  Thr Gln Glu Ser Gly  Ile Lys Glu
    1940                 1945                 1950

Ser Leu  Ser Trp Gly Thr Gln  Arg Thr Gln Asp Val  Leu Tyr Glu
    1955                 1960                 1965

Ala Arg  Ala Pro Leu Glu Arg  Gly His Ser Ala Glu  Ile Pro Val
    1970                 1975                 1980

Gly Gln  Pro Gly Ala Leu Ala  Val Asp Val Gln Met  Gln Asn Met
    1985                 1990                 1995

Thr Leu  Arg Gly Pro Asp Gly  Glu Pro Gln Pro Gly  Leu Glu Ser
    2000                 2005                 2010

Gln Gly  Arg Ala Ala Ser Met  Pro Arg Leu Ala Ala  Glu Thr Gln
    2015                 2020                 2025

Pro Ala  Pro Asn Ala Ser Pro  Met Lys Arg Ser Ile  Ser Thr Leu
    2030                 2035                 2040

Ala Pro  Arg Pro His Gly Thr  Gln Leu Cys Asn Thr  Val Leu Asp
    2045                 2050                 2055

Arg Pro  Pro Pro Ser Gln Val  Ser His His His His  His Arg Cys
    2060                 2065                 2070

His Arg  Arg Arg Asp Lys Lys  Gln Arg Ser Leu Glu  Lys Gly Pro
    2075                 2080                 2085

Ser Leu  Ser Val Asp Thr Glu  Gly Ala Pro Ser Thr  Ala Ala Gly
    2090                 2095                 2100

Ser Gly  Leu Pro His Gly Glu  Gly Ser Thr Gly Cys  Arg Arg Glu
    2105                 2110                 2115

Arg Lys  Gln Glu Arg Gly Arg  Ser Gln Glu Arg Arg  Gln Pro Ser
    2120                 2125                 2130

Ser Ser  Ser Ser Glu Lys Gln  Arg Phe Tyr Ser Cys  Asp Arg Phe
    2135                 2140                 2145
```

-continued

```
Gly Ser  Arg Glu Pro Pro Gln  Pro Lys Pro Ser Leu  Ser Ser His
    2150                 2155                 2160

Pro Ile  Ser Pro Thr Ala Ala  Leu Glu Pro Gly Pro  His Pro Gln
    2165                 2170                 2175

Gly Ser  Gly Ser Val Asn Gly  Ser Pro Leu Met Ser  Thr Ser Gly
    2180                 2185                 2190

Ala Ser  Thr Pro Gly Arg Gly  Gly Arg Arg Gln Leu  Pro Gln Thr
    2195                 2200                 2205

Pro Leu  Thr Pro Arg Pro Ser  Ile Thr Tyr Lys Thr  Ala Asn Ser
    2210                 2215                 2220

Ser Pro  Val His Phe Ala Glu  Gly Gln Ser Gly Leu  Pro Ala Phe
    2225                 2230                 2235

Ser Pro  Gly Arg Leu Ser Arg  Gly Leu Ser Glu His  Asn Ala Leu
    2240                 2245                 2250

Leu Gln  Lys Glu Pro Leu Ser  Gln Pro Leu Ala Ser  Gly Ser Arg
    2255                 2260                 2265

Ile Gly  Ser Asp Pro Tyr Leu  Gly Gln Arg Leu Asp  Ser Glu Ala
    2270                 2275                 2280

Ser Ala  His Asn Leu Pro Glu  Asp Thr Leu Thr Phe  Glu Glu Ala
    2285                 2290                 2295

Val Ala  Thr Asn Ser Gly Arg  Ser Ser Arg Thr Ser  Tyr Val Ser
    2300                 2305                 2310

Ser Leu  Thr Ser Gln Ser His  Pro Leu Arg Arg Val  Pro Asn Gly
    2315                 2320                 2325

Tyr His  Cys Thr Leu Gly Leu  Ser Thr Gly Val Arg  Ala Arg His
    2330                 2335                 2340

Ser Tyr  His His Pro Asp Gln  Asp His Trp Cys
    2345                 2350

<210> SEQ ID NO 7
<211> LENGTH: 27
<212> TYPE: PRT
<213> ORGANISM: Conus geographus
<220> FEATURE:
<221> NAME/KEY: MOD_RES
<222> LOCATION: 4, 10, 21
<223> OTHER INFORMATION: Xaa=hydroxyproline

<400> SEQUENCE: 7

Cys Lys Ser Xaa Gly Ser Ser Cys Ser Xaa Thr Ser Tyr Asn Cys Cys
1               5                   10                  15

Arg Ser Cys Asn Xaa Tyr Thr Lys Arg Cys Tyr
            20                  25
```